United States Patent
Reynolds et al.

(10) Patent No.: US 7,335,177 B2
(45) Date of Patent: Feb. 26, 2008

(54) ANKLE-FOOT ORTHOSIS

(75) Inventors: Ronan Reynolds, 2507 E. 15th St., Long Beach, CA (US) 90804; Guillermo Gustavo Weber, 1900 Coffee Port, Apt. H-2, Brownsville, TX (US) 78521; Roger Weber, 815 S. Los Robles Ave., Pasadena, CA (US) 91106; Samuel Landsberger, Rancho Palos Verdes, CA (US)

(73) Assignees: Ronan Reynolds, Longbeach, CA (US); Guillermo Gustavo Weber, Brownsville, TX (US); Roger Weber, Pasadena, CA (US)

(*) Notice: Subject to any disclaimer, the term of this patent is extended or adjusted under 35 U.S.C. 154(b) by 470 days.

(21) Appl. No.: 11/111,963

(22) Filed: Apr. 22, 2005

(65) Prior Publication Data

US 2005/0273028 A1    Dec. 8, 2005

Related U.S. Application Data

(60) Provisional application No. 60/564,728, filed on Apr. 23, 2004.

(51) Int. Cl.
*A61F 5/00* (2006.01)
(52) U.S. Cl. .......................... 602/23; 602/27
(58) Field of Classification Search ................ 128/882; 602/5, 16, 23, 27
See application file for complete search history.

(56) References Cited

U.S. PATENT DOCUMENTS

| | | |
|---|---|---|
| 453,475 A | 6/1891 | Harding |
| 1,232,899 A | 7/1917 | De Puy |
| 1,708,757 A | 4/1929 | Freileweh |
| 4,289,122 A | 9/1981 | Mason et al. |
| 4,454,871 A | 6/1984 | Mann et al. |
| 4,556,054 A | 12/1985 | Paulseth |
| 4,646,726 A | 3/1987 | Westin et al. |
| 4,651,726 A | 3/1987 | Holland |
| D297,368 S | 8/1988 | Womack |
| 4,862,900 A | 9/1989 | Hefele |
| 4,938,777 A | 7/1990 | Mason et al. |
| 5,038,762 A | 8/1991 | Hess et al. |
| 5,050,620 A | 9/1991 | Cooper |

(Continued)

FOREIGN PATENT DOCUMENTS

CA    2279225    8/1998

(Continued)

*Primary Examiner*—Michael A. Brown
(74) *Attorney, Agent, or Firm*—Arent Fox LLP

(57) ABSTRACT

An ankle-foot orthosis for aiding or enhancing a user's foot and ankle movement, wherein the orthosis comprises at least one strut member, a calf shell, a foot shell, and a plurality of segments. Gaps formed between adjacent segments, an uppermost segment and the calf shell, and a lowermost segment and the foot shell have gap widths, wherein gaps at a higher location have larger gap widths than those at a lower location. Therefore, in dorsiflexion, the gaps close in series from bottom to top, gradually increasing the orthosis stiffness, creating a progressive dorsiflexion stop, and decreasing the magnitude of loads transferred into the user. In plantar flexion, the gaps similarly decrease in series from bottom to top, gradually increasing the orthosis stiffness, creating a progressive plantar flexion stop, and decreasing the magnitude of loads transferred into the user.

24 Claims, 25 Drawing Sheets

U.S. PATENT DOCUMENTS

| | | | |
|---|---|---|---|
| 5,067,486 A | 11/1991 | Hely | |
| 5,088,479 A | 2/1992 | DeToro | |
| 5,199,941 A | 4/1993 | Makinen | |
| 5,393,303 A * | 2/1995 | Shiono | 602/27 |
| D358,891 S | 5/1995 | Miller | |
| 5,445,603 A | 8/1995 | Wilkerson | |
| 5,486,157 A | 1/1996 | DiBenedetto | |
| 5,501,659 A | 3/1996 | Morris et al. | |
| 5,609,568 A | 3/1997 | Andrews | |
| 5,716,336 A * | 2/1998 | Hines et al. | 602/27 |
| 5,759,168 A | 6/1998 | Bussell et al. | |
| 5,860,423 A | 1/1999 | Thompson | |
| 5,897,514 A * | 4/1999 | Currier | 602/16 |
| 5,897,515 A | 4/1999 | Wilner et al. | |
| 5,902,259 A | 5/1999 | Wilkerson | |
| 5,908,398 A | 6/1999 | DeToro | |
| 5,944,679 A | 8/1999 | DeToro | |
| D448,484 S | 9/2001 | Bradshaw | |
| 6,299,587 B1 | 10/2001 | Birmingham | |
| 6,302,858 B1 | 10/2001 | DeTorro et al. | |
| 6,319,218 B1 | 11/2001 | Birmingham | |
| 6,334,854 B1 | 1/2002 | Davis | |
| 6,676,618 B2 | 1/2004 | Andersen | |
| 6,689,081 B2 | 2/2004 | Bowman | |
| 6,692,454 B1 | 2/2004 | Townsend et al. | |
| 6,726,645 B1 | 4/2004 | Davis | |
| 6,752,774 B2 | 6/2004 | Townsend et al. | |
| D499,185 S | 11/2004 | Rabe | |
| 6,824,523 B2 | 11/2004 | Carlson | |
| 6,827,696 B1 | 12/2004 | Maguire | |
| D501,928 S | 2/2005 | Smits | |
| D503,480 S | 3/2005 | Ingimundarson et al. | |
| 6,860,864 B2 | 3/2005 | Meyer | |
| 6,887,213 B2 | 5/2005 | Smits | |
| 6,908,445 B2 | 6/2005 | Watts | |

FOREIGN PATENT DOCUMENTS

| | | |
|---|---|---|
| WO | WO02065942 | 8/2002 |

* cited by examiner

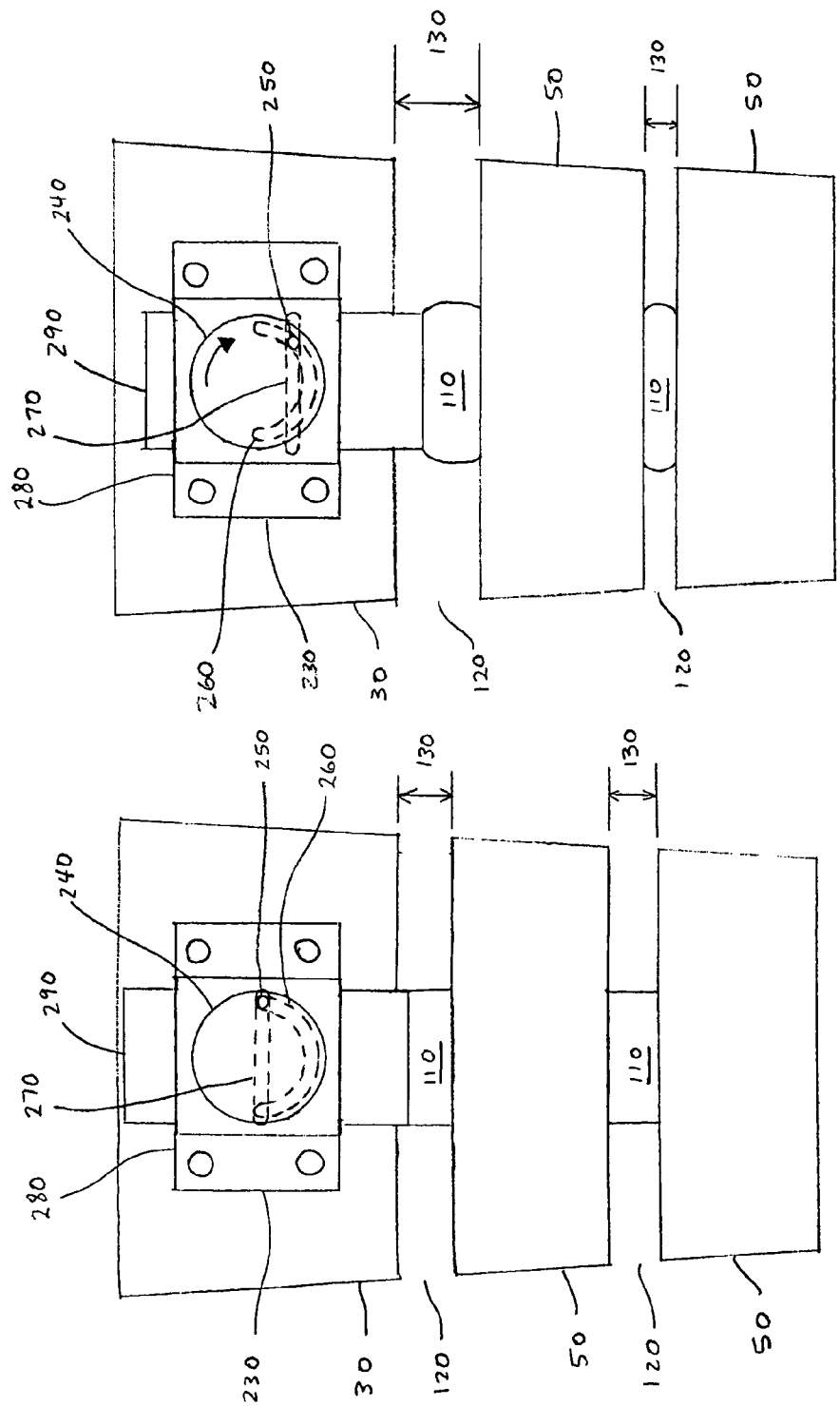

ANKLE-FOOT ORTHOSIS

CROSS-REFERENCE TO RELATED APPLICATION

This application claims the benefit of U.S. Provisional Application No. 60/564,728, filed Apr. 23, 2004.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. H133E003001 awarded by the U.S. Department of Education.

BACKGROUND OF THE INVENTION

1. Field of the Invention

The present invention relates to an improved ankle-foot orthosis for supporting the foot and ankle of a user. The orthosis of the present invention assists the user in plantar flexion and/or dorsiflexion extension of the user's foot while simultaneously controlling medial and lateral ankle stiffness as well as torsion of the ankle in the coronal plane.

2. Discussion of Related Art

Presently available ankle-foot orthoses are limited, because the orthoses cannot be customized to specifically address a specific user's dorsiflexion and plantar flexion stiffness needs to any significant or acceptable degree. The dorsiflexion stiffness of current orthoses is generally constant or decreases with increasing ankle angle, that is, the angle between a line passing between a user's knee and ankle and a horizontal line also passing through the ankle, as the foot dorsiflexes. The dorsiflexion stiffness of a normal human foot increases dramatically with increasing ankle angle. As a result, for users needing an orthosis that matches the dorsiflexion stiffness of the normal human foot, the presently available orthoses are unsatisfactory, leaving some users with reduced mobility and a decreased quality of life.

A further drawback of current orthoses relates to plantar flexion stiffness. An orthosis having low plantar flexion stiffness allows many users to walk more easily. However, currently available orthoses, other than some articulated orthoses, have a plantar flexion that is much higher, making walking and general mobility more difficult, and decreasing the user's quality of life. Additionally, dorsiflexion and plantar flexion stops, those features that prevent the orthoses from moving beyond a certain point in dorsiflexion and plantar flexion, respectively, provided in the presently available orthoses are rigid. Consequently, the stops cause the transmission of large forces into the user's body when the stops engage, and, over time, the relatively large forces damage a user's knee and hip joints.

SUMMARY OF THE INVENTION

The present invention addresses these problems, as well as others, by creating gradual dorsiflexion and plantar flexion stops as a user's foot is articulated in dorsiflexion and plantar flexion, respectively.

According to a first aspect of the invention, the present invention comprises at least one strut member, a calf shell disposed at an upper end of the at least one strut member, a foot shell disposed at a lower end of the at least one strut member, a plurality of segments disposed between the calf shell and the foot shell, gaps formed between two adjacent segments, an uppermost segment and the calf shell, and a lowermost segment and the foot shell, wherein, in dorsiflexion, a width of the gaps between front edges of the adjacent segments decreases until the front edges of the adjacent segments contact each other, increasing dorsiflexion stiffness and creating a gradual dorsiflexion stop, and further wherein, in plantar flexion, a width of the gaps at back edges of the adjacent segments decreases, increasing plantar flexion stiffness and creating a gradual plantar flexion stop.

According to a second aspect of the invention, spacers are disposed within the gaps, wherein the spacers compress in dorsiflexion and plantar flexion as the widths of the gaps at the front and back edges decrease, causing the stiffness of the orthosis to increase. Further, in a preferred embodiment, the gaps progressively increase in width from a lower end of the orthosis to an upper end wherein the gaps at the lower end are narrower than the gaps at the upper end. Therefore, in dorsiflexion or plantar flexion, the gaps close in series beginning at the lower end, wherein a gradual dorsiflexion or plantar flexion stop is formed.

According to a third aspect of the invention, front edges of the segments contact each other during dorsiflexion, wherein the effective length of a flexing portion of the orthosis is reduced, which causes the orthosis stiffness to increase according to well known and understood beam bending principles. In plantar flexion, according to an embodiment, rear edges of the segments also contact each other, wherein the effective length of a flexing portion of the orthosis is reduced, causing the orthosis stiffness to increase according to well known and understood beam bending principles. In an alternate embodiment having spacers provided within the gaps, the rear edges of the segments come into contact during plantar flexion, compressing the spacers therebetween, changing the effective length of the flexing portion, and increasing the plantar flexion stiffness.

According to a fourth aspect of the invention, the ankle-foot orthosis includes a hinge between, for example, the foot shell and a lowermost segment, wherein the hinge eliminates substantially all stiffness of the orthosis in both plantar flexion and dorsiflexion at a location where the hinge is provided.

According to a fifth aspect of the present invention, the ankle-foot orthosis includes elastic members extending from the calf shell to the foot shell to provide a dorsiflexion bias. According to a preferred embodiment, the elastic members extend through coincident openings in a front portion of the segments.

According to a sixth aspect of the invention, the foot shell includes a toe extension at a front end thereof.

According to a seventh aspect of the invention, the ankle-foot orthosis includes straps for securing the orthosis to the user.

According to a eighth aspect of the invention, the ankle-foot orthosis includes a liner provided on a surface of the orthosis that contacts a posterior surface of a lower leg and a lower foot surface of a user.

According to an ninth aspect of the invention, the ankle-foot orthosis further includes an adjustment mechanism provided between the calf shell and an uppermost segment for expanding or narrowing the width of the gap therebetween. Expanding the width of the gap in which the adjustment mechanism is provided correspondingly narrows the widths of the gaps therebelow, compresses the spacers disposed between opposing surfaces defining the gaps, and increases the stiffness the orthosis. Narrowing the width of the gap in which the adjustment mechanism is provided correspondingly expands the widths of the gaps therebelow, decompresses the spacers disposed between the opposing surfaces defining the gaps, and decreases the stiffness of the orthosis. In one embodiment, the adjustment mechanism is a threaded rod and locknut combination. Alternately, the adjustment mechanism is a twist draw mechanism.

According to a tenth aspect of the present invention, an alternate embodiment of the ankle-foot orthosis includes a strut member, a calf shell disposed at an upper end of the strut member, a foot shell disposed at a lower end strut member, and a plurality of segments disposed between the calf shell and the foot shell along front and back surfaces of the strut member forming gaps therebetween. In dorsiflexion, a width of the gaps at front edges thereof decrease until the front edges of the segments contact each other, increasing dorsiflexion stiffness and creating a gradual dorsiflexion stop. In plantar flexion, a width of the gaps at back edges thereof decreases, increasing plantar flexion stiffness and creating a gradual plantar flexion stop.

In a further embodiment, the segments are integrally formed on the front and back surface in the strut member. Alternately, the segments are secured to the front and back surfaces of the strut member by fasteners or an adhesive.

In a preferred embodiment, the gaps progressively increase in width from a lower end of the orthosis to an upper end wherein the gaps at the lower end are narrower than the gaps at the upper end. Therefore, in dorsiflexion or plantar flexion, the gaps close in series, beginning at the lower end to define a gradual dorsiflexion and plantar flexion stop. Further, the foot shell includes an optional toe extension and straps for securing the orthosis to the user.

It is an additional aspect of this invention to be incorporated into various types of footwear for non-disabled users, wherein the invention would perform the function of the calf muscle to reduce muscle fatigue and enhance physical performance of the user, such as endurance.

Additional aspects, advantages, and novel features of the invention will be better understood as set forth in the following description and accompanying drawings and will also become apparent to those skilled in the art upon examination of the following or upon learning by practice of the invention.

BRIEF DESCRIPTION OF DRAWINGS

FIG. 10 is an enlarged view of a second embodiment of an adjustment mechanism of the present invention;

FIG. 11 is an enlarged view of the adjustment mechanism shown in FIG. 10, wherein the adjustment mechanism is in an extended state;

DETAILED DESCRIPTION OF THE INVENTION

The present invention relates to an ankle-foot orthosis ("orthosis") worn by a user on a lower leg and ankle region of the user's body. The orthosis supports and assists users who have difficulty in manipulating a foot in dorsiflexion and plantar flexion. Additionally, a user having no such difficulty can use the orthosis to assist normal plantar flexion and dorsiflexion movement of the user's lower leg and foot, which may enhance the user's performance and endurance of the lower leg and foot.

Figure 1:
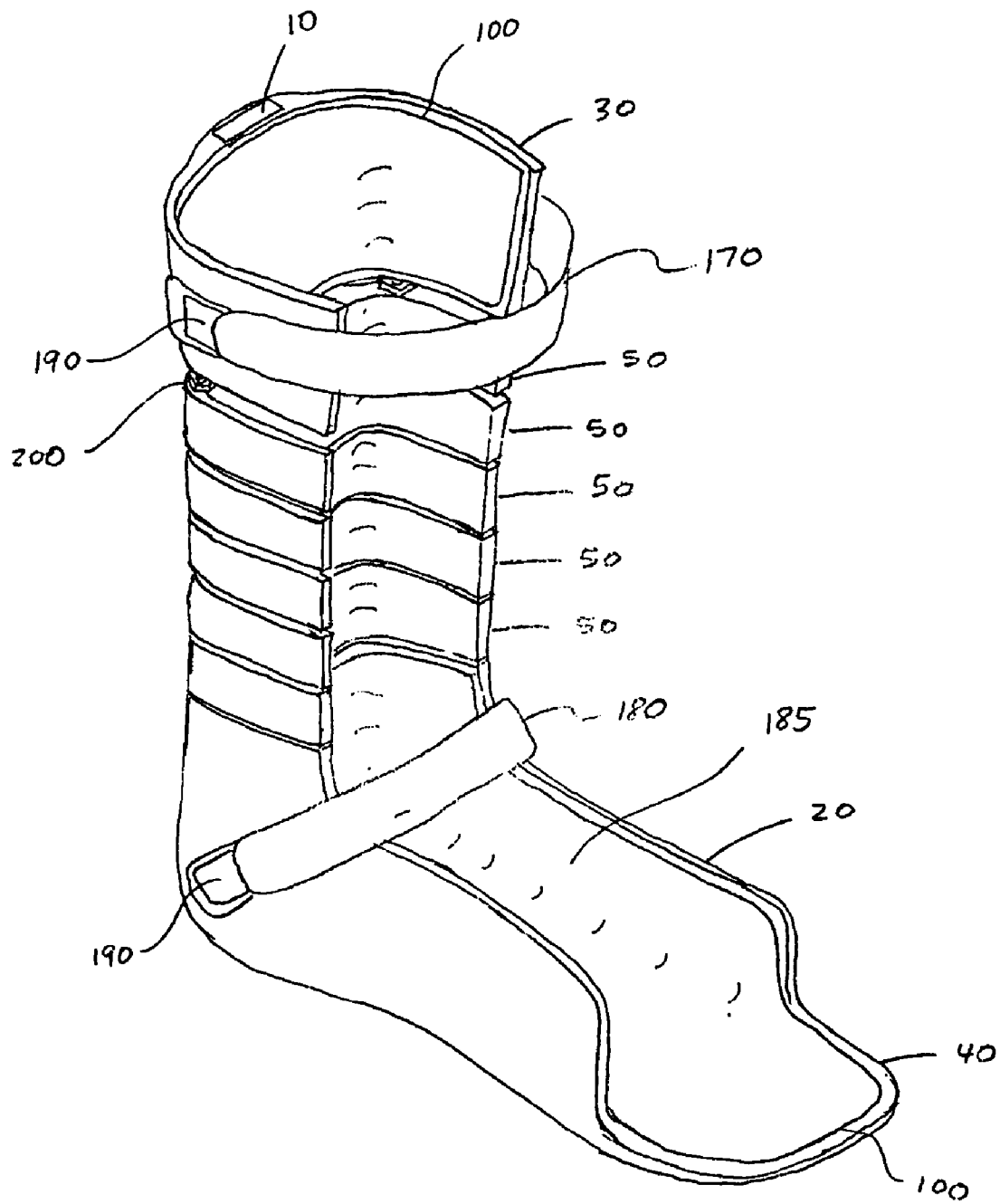
FIG. 1 is a perspective view of an ankle-foot orthosis device according to a first embodiment of the present invention.
Figure 2:
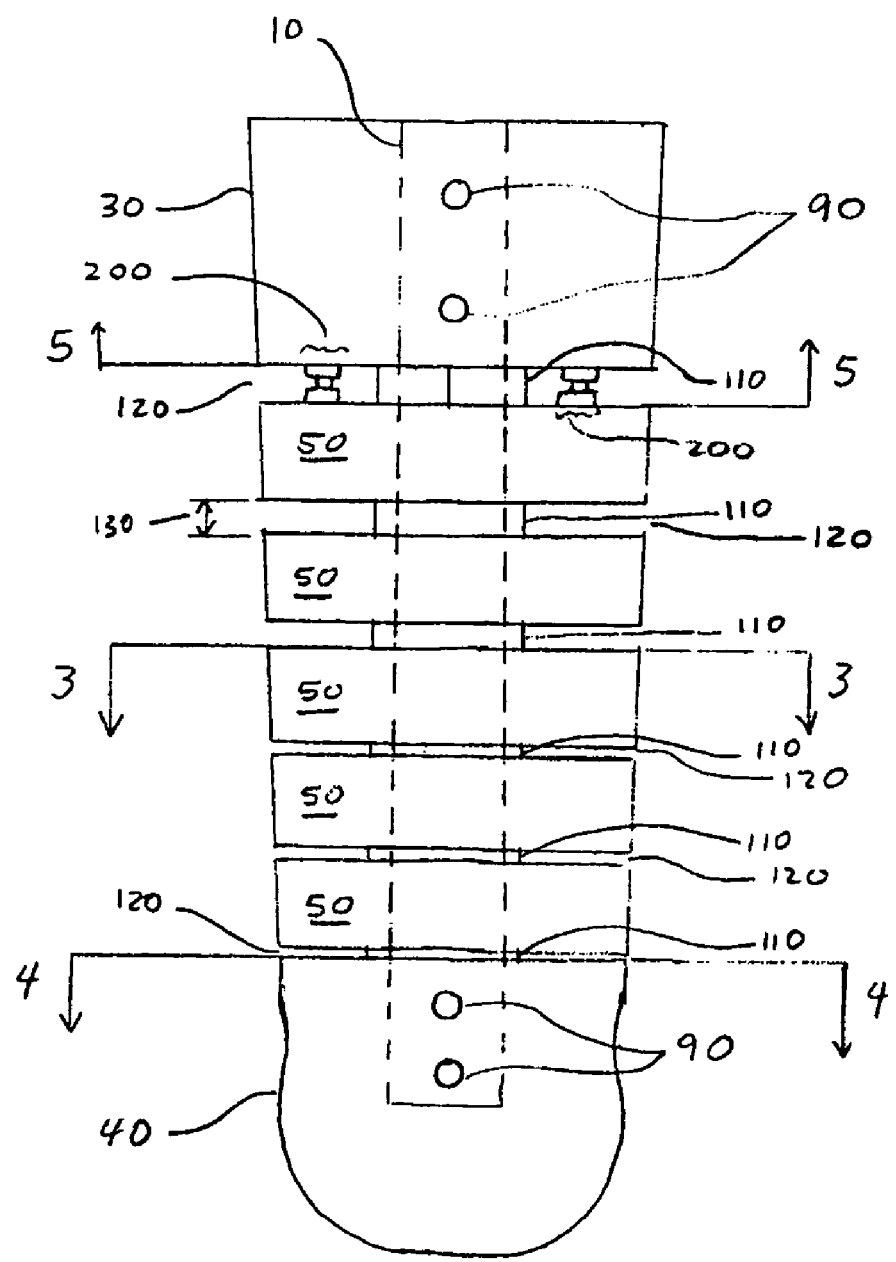
FIG. 2 is a back view of the ankle-foot orthosis shown in FIG. 1.

FIGS. 1 and 2 illustrate an orthosis according to a first embodiment of the present invention. The orthosis includes a strut 10 having a foot shell 20 attached to a lower end and a calf shell 30 attached to an upper end. Optionally, the foot shell 20 may include a toe extension 40 for supporting a user's toes, if such support is needed by the user. A plurality of segments 50 extends from the calf shell 30 to the foot shell 20 along a vertical length of the strut 10. In a preferred embodiment, the foot shell 20, calf shell 30, and segments 50 have U-shaped cross-sections. Further, the orthosis includes an adjustment mechanism 200 for adjusting the stiffness of the orthosis, which is described in more detail below.

Figure 3:
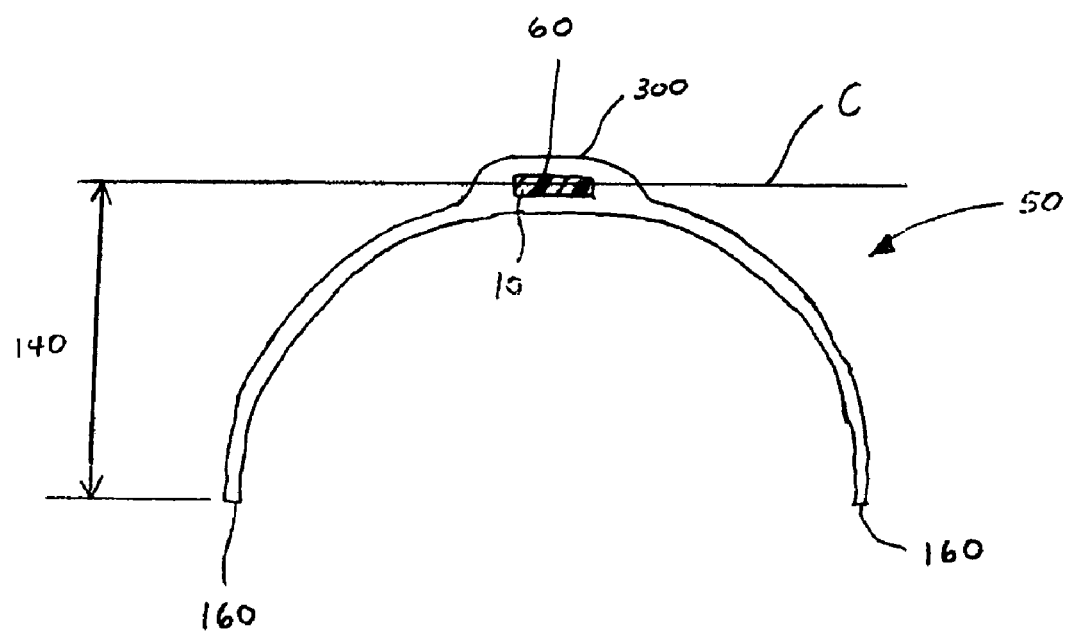
FIG. 3 is a view taken along line 3-3 in FIG. 1.
Figure 4:
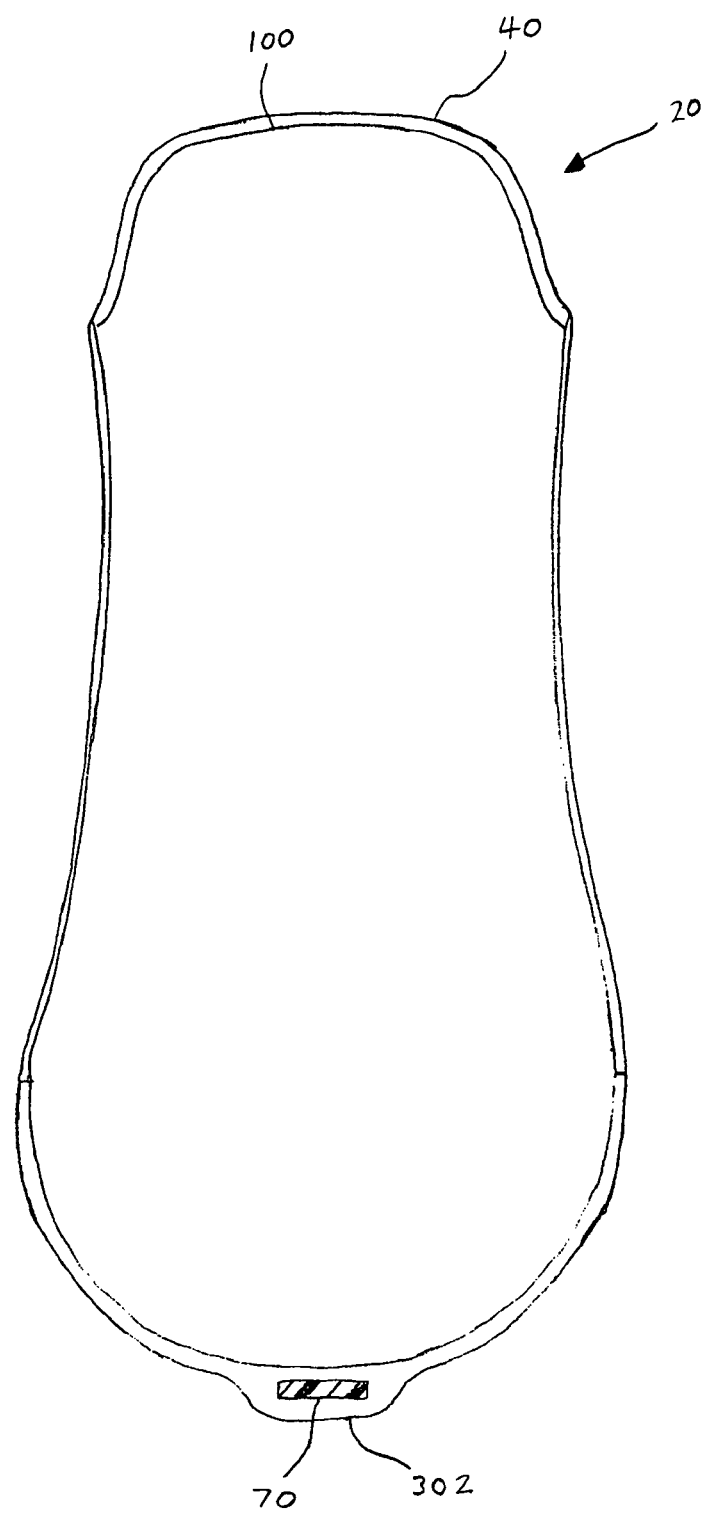
FIG. 4 is a view taken along line 4-4 in FIG. 1.

Referring to FIG. 3, the segment 50 includes a passageway 60 extending vertically through a back portion thereof, a pair of front edges 160, and a back edge 300. The passageway 60 is configured to accommodate a portion of the strut 10 passing therethrough. As shown in FIG. 4, the foot shell 20 also includes an opening 70 extending through a back portion thereof, the optional toe extension 40, a liner 100, and a back edge 302. As with the segment 50, the passageway 70 of the foot shell 20 is configured to accommodate a lowermost portion of the strut 10 thereon.

Figure 5:
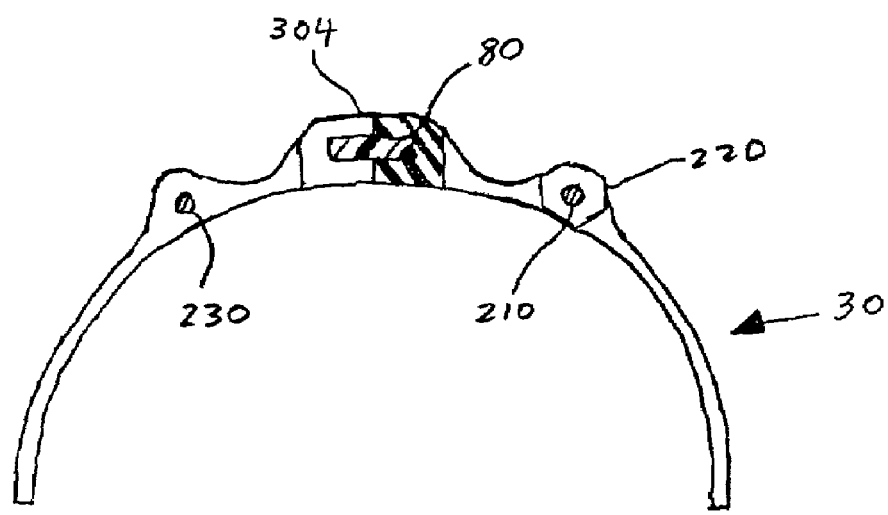
FIG. 5 is a view taken along line 5-5 in FIG. 1.

FIG. 5 illustrates a bottom view of the calf shell 30, which includes a passageway 80 extending vertically through a posterior portion thereof and a back edge 304. A lower end of the strut 10 is insertable into the opening 70, while an upper end of the strut 10 is insertable into the passageway 80. Preferably, the foot shell 20 and the calf shell 30 fixably attach to the strut 10 via fasteners 90, as illustrated in FIG. 2. However, it is within the scope of the invention that the strut 10 be fixably attached to at least one of the foot shell 20 and calf shell 30 with, for example, an adhesive or by being insert molded therein at the time of manufacture. It is also within the scope of the invention to fittably attach the strut to the foot shell 20 and/or the calf shell 30 via any other suitable known, or future developed, manner Referring to FIG. 1, a liner 100 is secured to an upper surface of the foot shell 20, anterior surfaces of the calf shell 30 (not shown), and anterior surfaces of the segments 50 (not shown). Preferably, the liner 100 is a relatively thin padding material that conforms to the user, providing a comfortable form fit and cushioning. The liner 100 also reduces rubbing between the orthosis and user's lower leg and foot, to improve the comfort of the orthosis. Further, the portion of the liner 100 attached to the calf shell 30 helps prevent the user's lower leg from being pinched between neighboring segments 50. Ideally, the liner 100 attaches to the orthosis by an adhesive, for example.

In one embodiment, the strut 10 is a long, slender member having a rectangular cross-section. However, it is within the scope of the present invention that the cross-section of the strut 10 be circular, semi-circular, crescent, trapezoidal, triangular, pentagonal, hexagonal, elliptical, or any suitable geometric shape. Further, in a preferred embodiment, the strut 10 is formed from a Garolite® compression molded carbon fiber epoxy laminate or a pultruded carbon fiber epoxy composite rod, each of which has a high rigidity and is relatively lightweight. However, it is within the scope of the present invention that the strut 10 can be formed from any material having suitable rigidity. Such materials include, for example only, a metal or a polymer, such as, for example, polyethylene or deldrin. The material selected for the strut 10 depends upon the amount of rigidity needed by the user. The foot shell 20, calf shell 30, and segments 50 are formed from a composite material, such as fiberglass or a carbon fiber epoxy composite. However, polymers such as, for example, polyethylene or polypropylene can also be used to form the foot shell 20, calf shell 30, and the segments 50.

Referring to FIG. 2, a spacer 110 is provided between adjacent segments 50; between an uppermost segment 50 and the calf shell 30; and between a lowermost segment 50 and the foot shell 20, with gaps 120 formed therebetween. Each gap 120 has a gap width 130 and a gap length 140 as shown in FIGS. 2 and 3, respectively.

Figure 6:
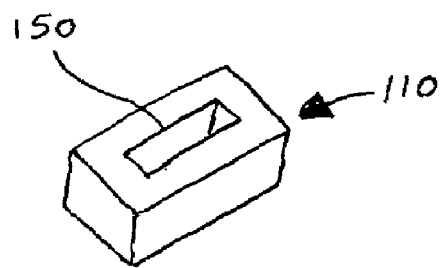
FIG. 6 is a perspective view of a first embodiment of a spacer of the ankle-foot orthosis shown in FIG. 1.

FIG. 6 illustrates an exemplary embodiment of the spacer 110 having a vertically extending passageway 150 through a central portion thereof. The strut 10 extends through the passageway 150, wherein each spacer 110 surrounds a portion of the outer periphery of the strut 10. The gap width 130 generally corresponds to a vertical thickness of the corresponding spacer 110. The gap length 140, illustrated in FIG. 3, is measured perpendicularly from a line C provided on a surface of strut 10 that is normal to the front edge 160 of the segment 50.

Figures 2A, 2B:
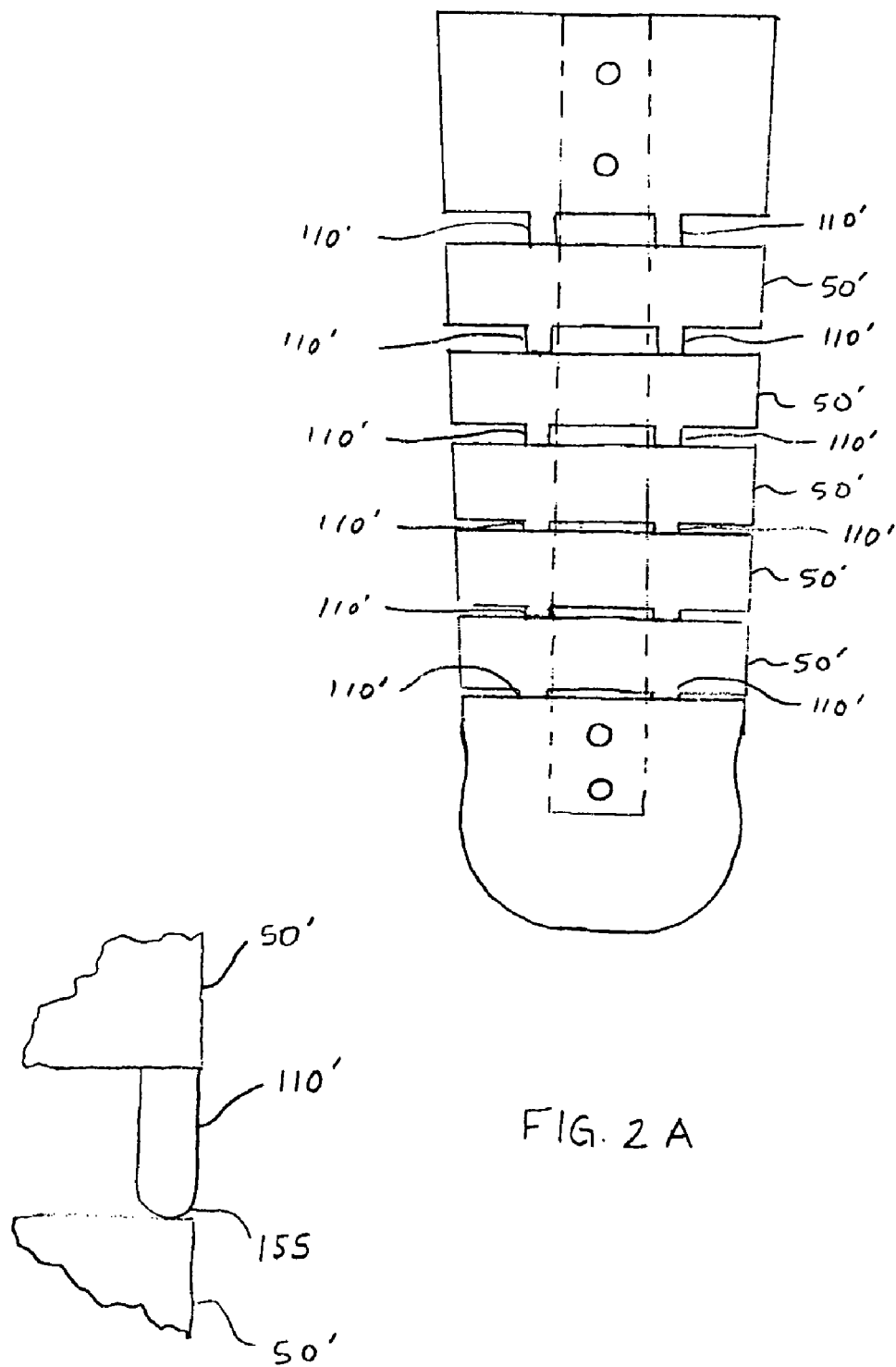
FIG. 2A is a back view of the ankle-foot orthosis having spacers formed on corresponding segments.
FIG. 2B is a detailed view of the spacers formed on the corresponding segments shown in FIG. 2A.

Alternately, spacers 110' are integrally formed on a corresponding segment 50', as illustrated in FIG. 2A. The spacers 110' include a rounded edge 155 that rollingly engages a neighboring 50', as illustrated in FIG. 2B.

The material used for the spacers 110 can be selected depending on the intended use or needs of the user. Where a low rigidity is desired or needed, the spacers 110 can be formed from a flexible material, such as, for example only, rubber. Alternatively, a metal, such as, for example only, steel or aluminum, or a stiff plastic, such as, for example only, polyethylene, can be used when a higher rigidity is desired and/or needed. However, it is within the scope of the present invention to use any suitable material for the spacers 110. Additionally, while the spacer 110 is illustrated in FIG. 6 as having a rectangular shape, it is within the scope of the invention that the spacers 110 can have any shape, such as, for example only, triangular, trapezoidal, crescent, circular, semi-circular, pentagonal, elliptical and hexagonal.

In a preferred embodiment, each gap width 130 is wider than the gap width 130 immediately thereunder but narrower than the gap width immediately thereabove. However, it is within the scope of the invention that the gap widths 130 be of any size, such as, for example only, the gap widths 130 could be of equal widths or varying widths.

An upper surface of the foot shell 20 can be generically shaped or custom fit to a lower surface of a user's foot. A front surface of the calf shell 30 is configured to abut a posterior of a user's lower leg and can also be generically shaped or custom fit according to the dimensions of the user's leg.

Referring to FIG. 1, straps 170 and 180 are provided on the foot and calf shells 20 and 30, respectively, for securing the orthosis to the user's leg. The straps 170 and 180 are secured to the orthosis on one side of a front opening 185 of the orthosis. An attachment mechanism 190 removably secures the straps 170 and 180 to respective mating surfaces on an opposite side of the front opening 185 to secure the orthosis to the user.

In a preferred embodiment, the attachment mechanism 190 includes a hook and loop fastener, wherein one end of strap 180 attaches to the calf shell 30, such as with an adhesive or fasteners (not shown), and wraps around an anterior of the lower leg. A second end of the strap 180 includes the hook and loop fastener on an inner surface thereof that engages a corresponding hook and loop fastener provided, for example, on an outer surface of the calf shell 30 or on an outer surface of the strap 80 to secure the lower leg into the calf shell 30.

Figure 7:
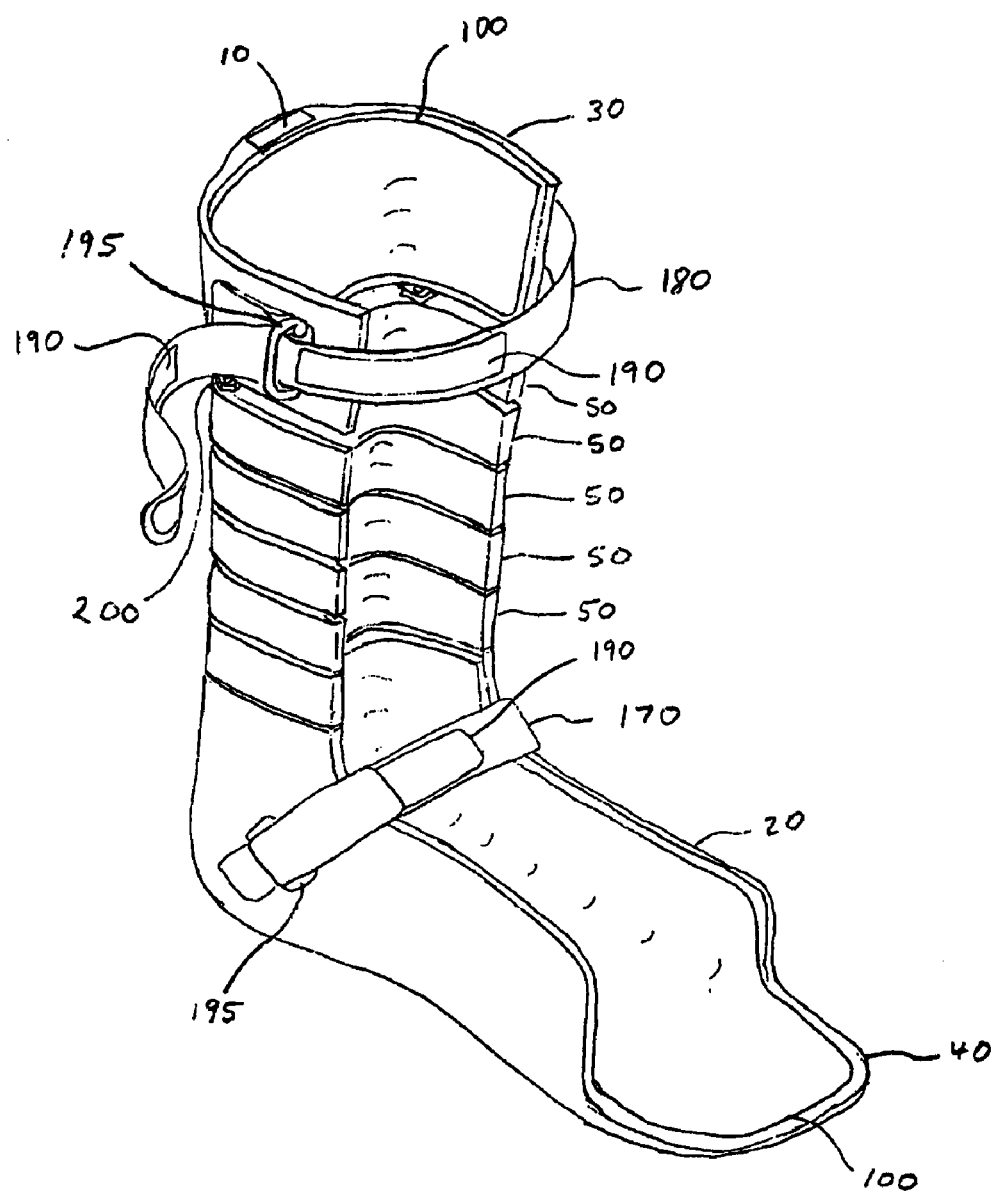
FIG. 7 is a perspective view of an ankle-foot orthosis according to second embodiment of the present invention.

In an alternate embodiment as shown in FIG. 7, the strap 180 wraps around the anterior of the lower leg, passes through a loop 195 affixed to the calf shell 30 and then folds back over an upper surface of the strap 180, wherein a hook and loop fastener on an outer strap surface near a free end of the strap 80 engages a corresponding hook and loop fastener also on the outer strap surface. Other examples of the attachment mechanism 190 include, for example only, snap fasteners or a buckle. However, it is within the scope of the invention that the attachment mechanism 190 be any structure now in existence or hereafter developed that is capable of securing the calf shell 30 to a user's lower leg.

Again referring to FIG. 1, the strap 170 is positioned near a back end of the foot shell 20 and at approximately a 45° angle from horizontal wherein the strap 170 wraps over an upper surface of the user's foot near the ankle region.

Ideally, the attachment mechanism 190 for securing the strap 170 is identical to that used for the strap 180. However, it is within the scope of the present invention that the strap 170 use an attachment mechanism 190 different from that used with the strap 180, be located anywhere on the foot shell 20, and be positioned at any angle. It is also within the scope of the invention to provide additional straps and corresponding attachment mechanisms, such as those disclosed above, at other locations on the orthosis to secure the orthosis to a user. Once strapped on, the user can thereafter put on an article of footwear. Alternately, the orthosis could be integral to an article of footwear.

Figures 8, 9:
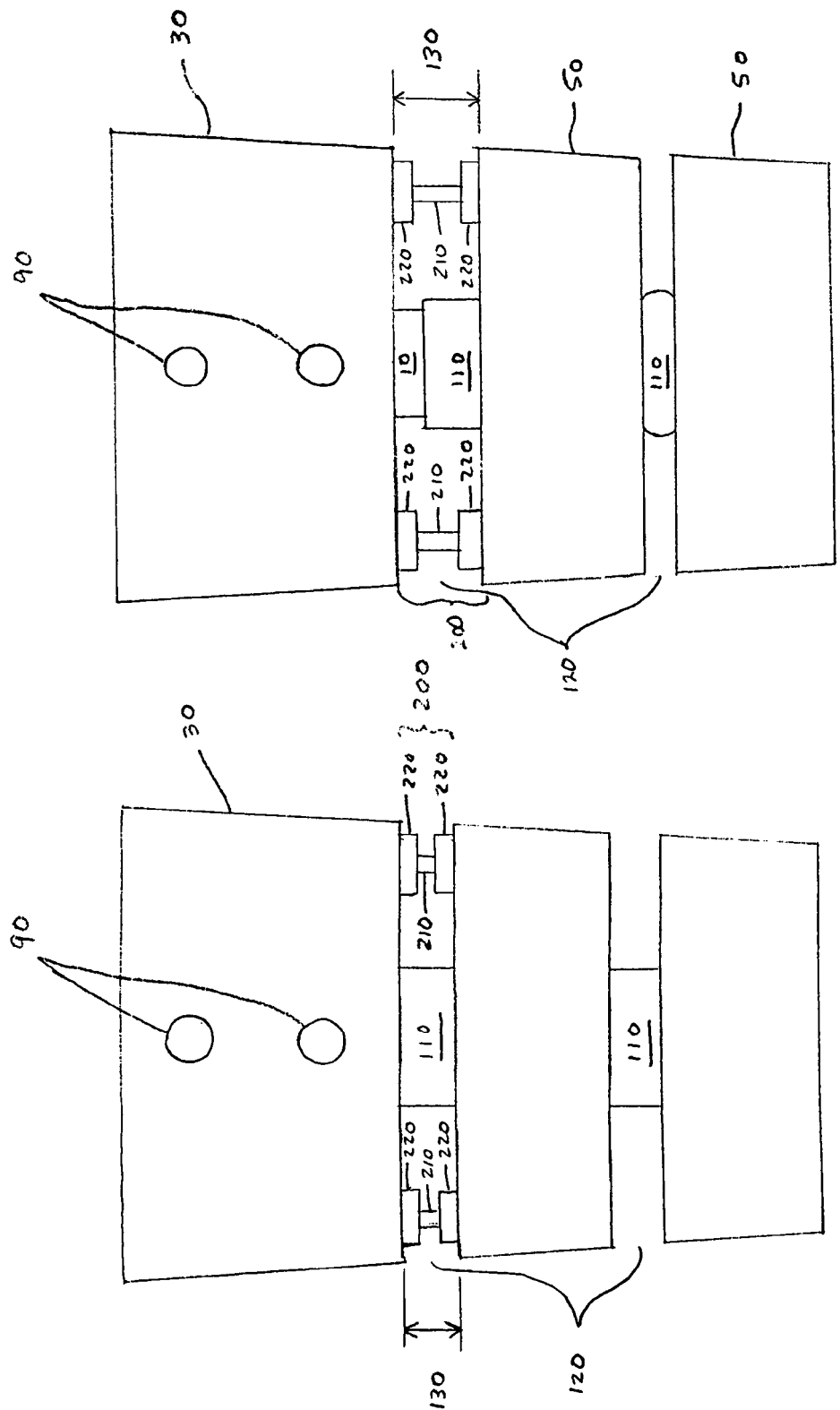
FIG. 8 is an enlarged view of a first embodiment of an adjustment mechanism of the present invention.
FIG. 9 is an enlarged view of the adjustment mechanism shown in FIG. 8, wherein the adjustment mechanism is in an extended state.

The adjustment mechanism 200 for adjusting the stiffness of the orthosis is now described. Referring to FIGS. 8-9, one embodiment of the adjustment mechanism 200 includes threaded rods 210 and locknuts 220. The threaded rods 210 are retained within openings 230 provided in a lower surface of the calf shell 30 and coaxial openings provided in an upper surface of the segment 50 adjacent to the calf shell 30. The locknuts 220 are raised and lowered over the threaded rods 210 by rotating the locknuts 220 clockwise or counterclockwise. One locknut 220 abuts the lower surface of the calf shell 30 while a second locknut 220 abuts the upper surface of the adjacent segment 50.

When the locknuts 220 are rotated, wherein the locknuts 220 to move in opposite directions away from each other, the calf shell 30 and adjacent segment 50 correspondingly move away from each other, compressing the spacers 110 in the gaps 120 above and below the adjustment mechanism 200. The calf shell 30 and adjacent segment 50 will continue to move away from each other only to the extent the spacers 110 are compressible. By adjusting the locknuts 220 in this manner, the orthosis becomes stiffer because the spacers 110 are compressed and front edges 160 of the segments 50 come into contact sooner as the user's foot dorsiflexes and a range of motion of the user's ankle in both dorsiflexion and plantar flexion is reduced.

Alternatively, when the locknuts 220 are rotated causing the locknuts 220 to move towards each other, the calf shell 30 and adjacent segment 50 move towards each other. The calf shell 30 and adjacent segment 50 will continue to move towards each other only until the lower surface of the calf shell 30 and the upper surface of the adjacent segment 50 contact the spacer 110. Therefore, as the locknuts 220 move towards each other, the spacers 110 become less compressed, the gap widths 130 of gaps 120 increase, and the segments 50 move upwards along the strut 10 causing the orthosis to become less stiff. Moreover, the range of motion of the user's ankle in both dorsiflexion and plantar flexion increases. While the above-described embodiment of the adjustment mechanism is provided in the gap 120 between the calf shell 30 and adjacent segment 50, it is within the scope of the present invention that the adjustment mechanism 200 comprising the threaded rods 210 and locknuts 220 could be located within other gaps 120.

FIGS. 10 and 11 illustrate a second embodiment of the adjustment mechanism 200', which includes a twist draw mechanism 230. The mechanism 230 is essentially a twist draw latch, sometimes referred to as a butterfly latch. In one embodiment of the mechanism 230, a rotatable member 240 causes a pin 250 attached at a radius of the rotatable member 240 to slide within a slots 260 and 270 provided in a frame member 280 and a slide 290, respectively. The slot 260 restricts the amount of rotation that rotatable member 240 may rotate. The slide 290 is constrained horizontally but not vertically. Therefore, as the pin 250 follows a circular motion of the rotatable member 240 within slot 260, the pin 250 freely moves horizontally within the slot 270, forcing the slide 290 to move vertically within the frame member 280. As a result, the circular motion is translated into a purely vertical motion. Consequently, when the mechanism 230 is attached to the posterior of the calf shell 30, for example, a lower edge of the slide 290 abuts an upper surface of the adjacent spacer 110. When the rotatable member 240 is turned, the slide 290 moves downward, compressing the spacer 110, forcing the adjacent segment 50 downward, and so on. As a result, the gap widths 130 of the gaps 120 below the mechanism 230 decrease, making the orthosis stiffer and reducing the range of motion of the user's ankle in both dorsiflexion and plantar flexion.

While an exemplary embodiment of the twist draw mechanism 230 is disclosed above, one of ordinary skill in the art would recognize other obvious iterations thereof. Accordingly, the present invention extends to all such embodiments of the twist draw mechanism 230. Further, the adjustment mechanism 200 and 200' is not limited to the two above-described embodiments but, rather, extends to any and all structure now in existence or hereafter created capable of changing the gaps widths 130 of the gaps 120.

Figure 12:
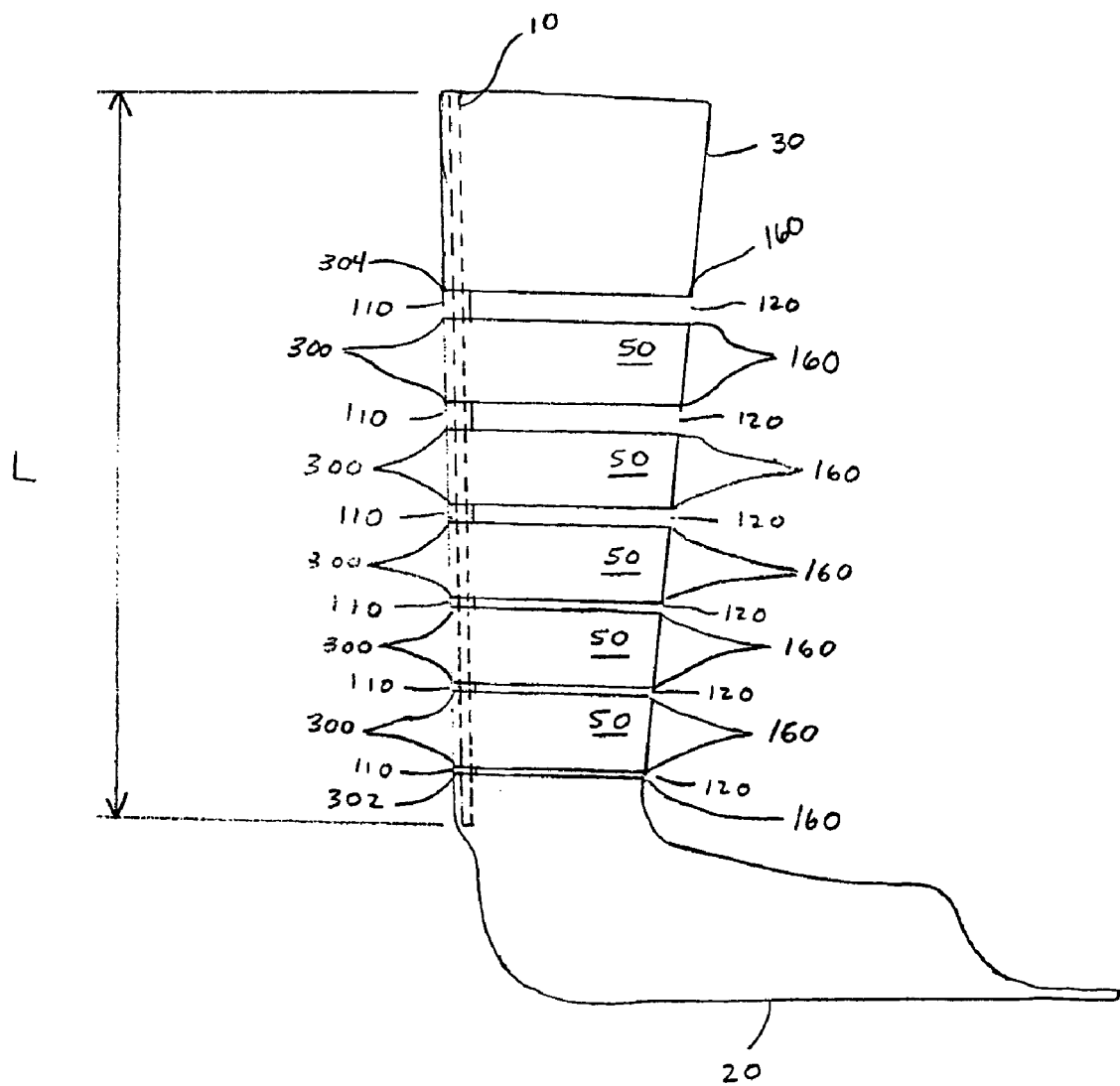
FIG. 12 is a side view of an ankle-foot orthosis according to the first embodiment of the present invention.

Referring to FIG. 12, a flexing portion of the orthosis including the strut 10, the calf shell 30, the segments 50, and spacers 110 forms a beam having an effective length L. As the user's foot dorsiflexes, the gap widths 130 decrease progressively along the gap length 140 (FIG. 3), compressing the spacers 50, wherein the greatest decrease in the gap widths 130 occurs at the front edges 160. Because the gap widths 130 at a lower end of the orthosis are narrower than those higher up, the front edges 160 of the lowermost segment 40 and foot shell 20 begin contacting each other sooner, changing the effective length L of the beam. The change in effective length L causes an increase in stiffness according to beam bending principles known to those of ordinary skill in the art. As the gaps 120 higher up, i.e., further from the foot shell 20, continue to close at the front edges 160, the effective length L continues to progressively decrease, making the orthosis stiffer, creating a gradual dorsiflexion stop, and reducing the magnitude of any forces transmitted through the user's body.

Referring to FIGS. 3-4 and 12, in plantar flexion, the rear edge 300 of the lowermost segment 50 is forced towards the rear edge 302 of the foot shell 20. The rear edges 300 of adjacent segments 50 are also forced towards each other. Further, the rear edge 300 of the uppermost segment 50 is also forced toward the rear edge 304 of the calf shell 30. Consequently, the gaps 120 narrow, compressing the spacers 110 provided therein. Initially, the lowermost gap 120 adjacent to the foot shell 20 and having the smallest gap width 130 decreases until the spacer 110 provided therein can no longer be compressed. Next, the gap 120 immediately above stops closing, because the spacer 110 provided therein can also no longer be compressed. Thereafter, the gaps 120 thereabove similarly stop closing in order, beginning with the lower, narrower gaps 120 and finishing with the larger gaps 120 near the calf shell 30. Therefore, as plantar flexion increases, the effective length L of the flexing portion decreases, causing the orthosis to progressively become stiffer. Further, changing the effective length L creates a gradual plantar flexion stop and reduces the magnitude of any forces transmitted through the user's body.

Figure 13:
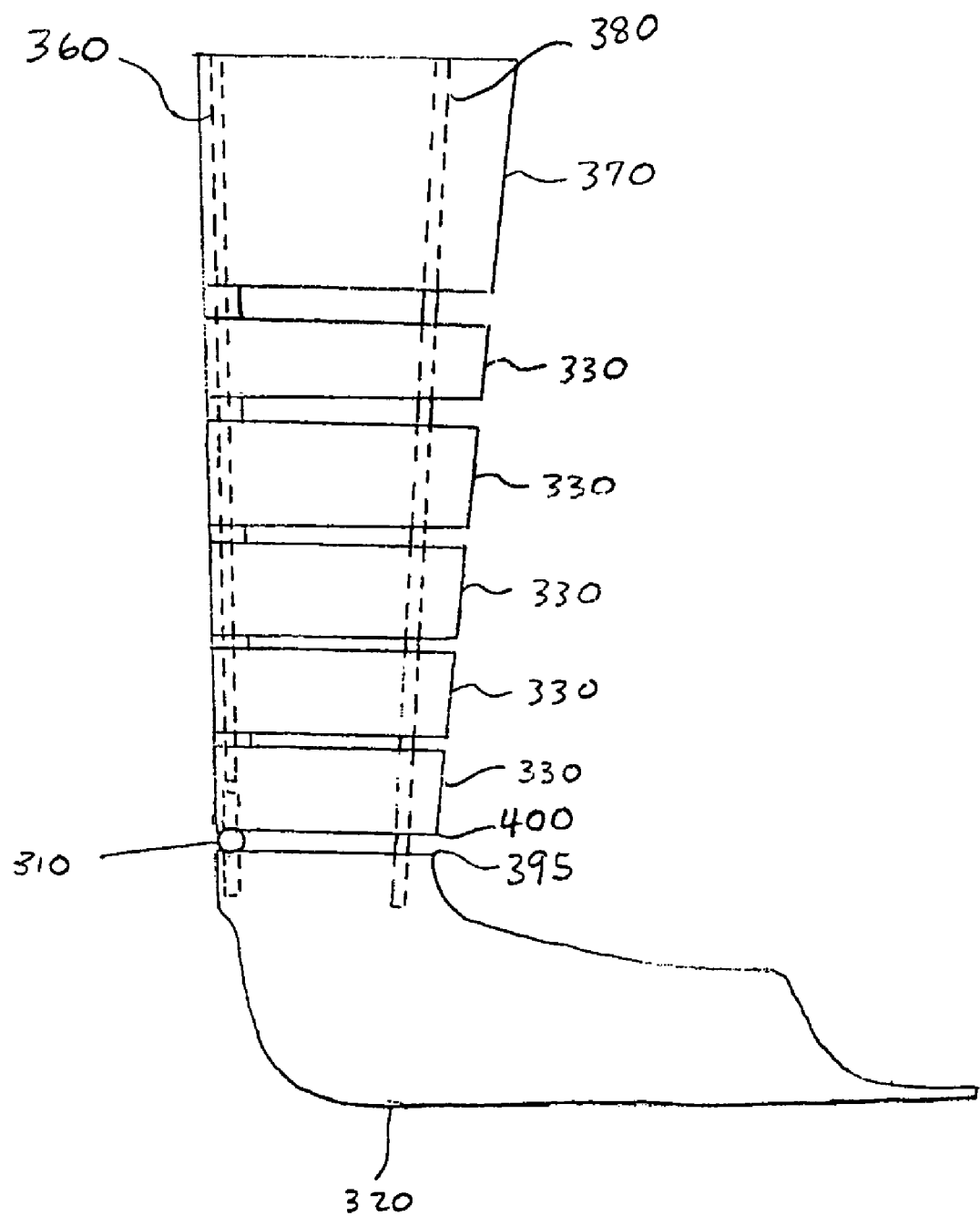
FIG. 13 is a side view of an ankle-foot orthosis according to a third embodiment of the present invention.
Figure 14:
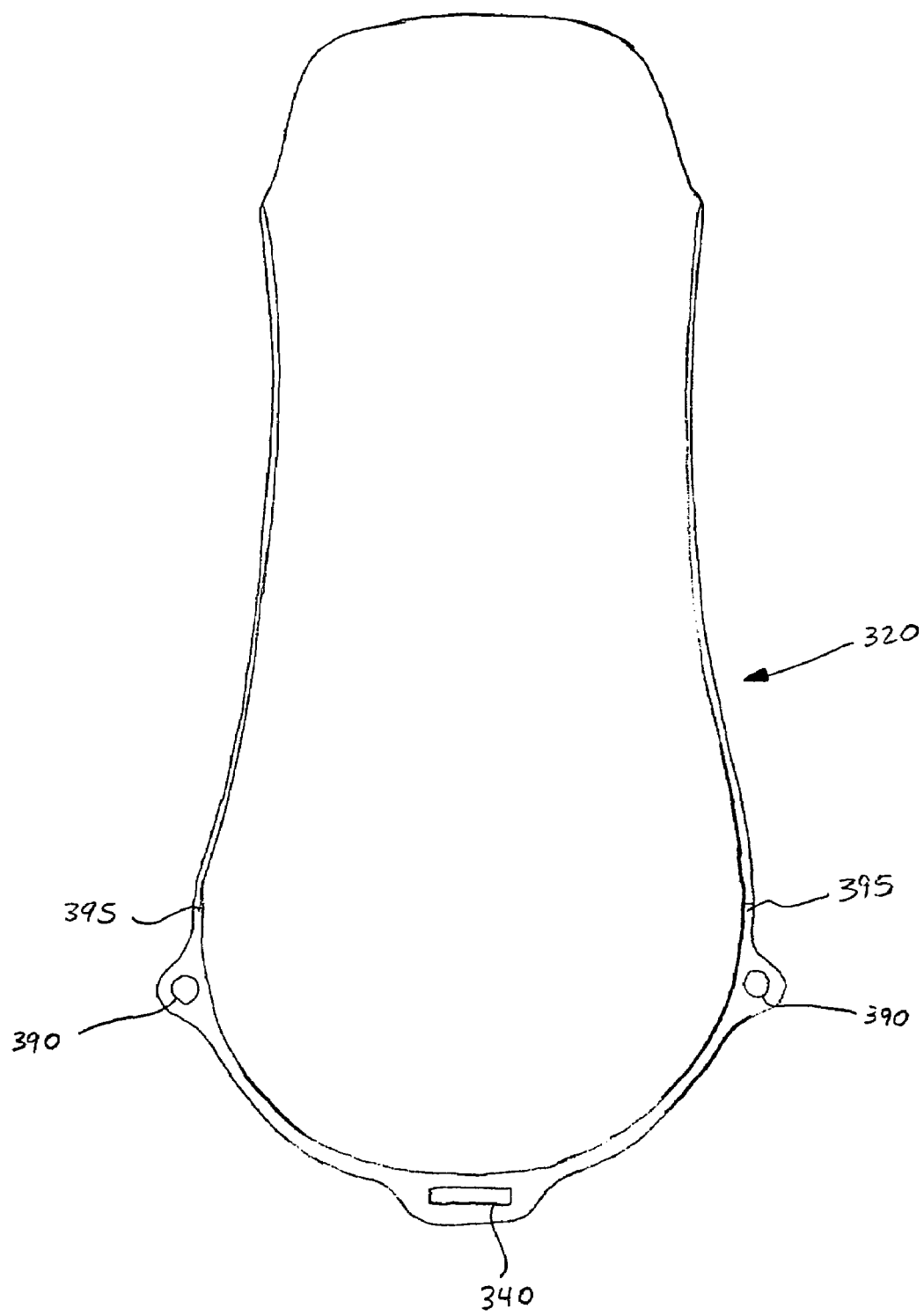
FIG. 14 is a top view of a foot shell of the ankle-foot orthosis shown in FIG. 13.
Figure 16:
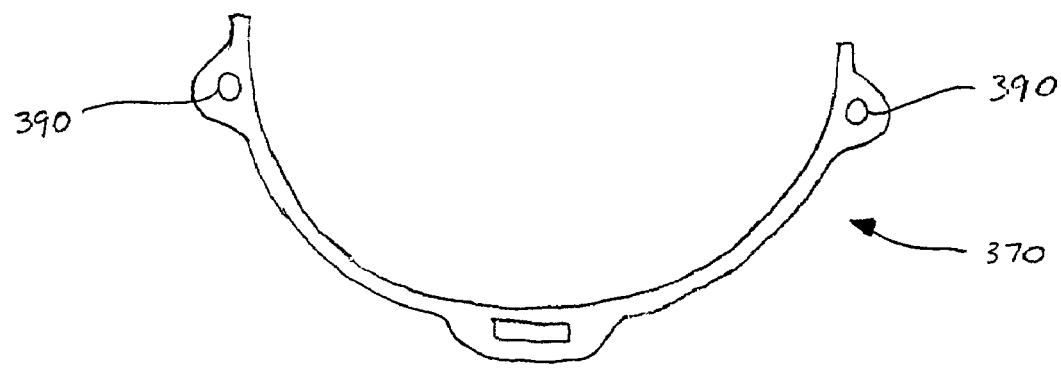
FIG. 16 is a top view of a calf shell of the ankle-foot orthosis shown in FIG. 13.
Figure 15:
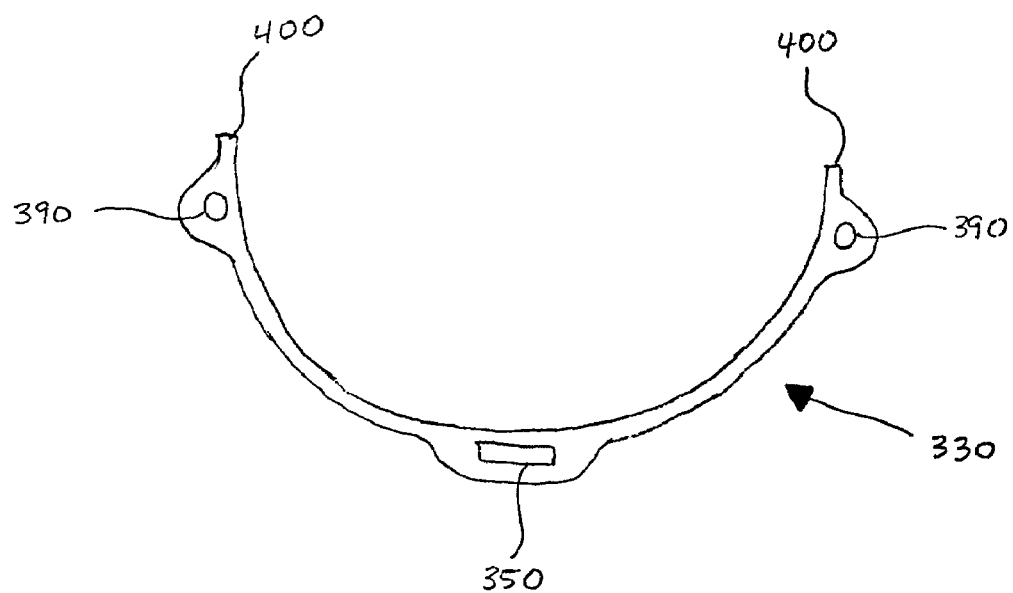
FIG. 15 is a top view of a segment of the ankle-foot orthosis shown in FIG. 13.
Figure 17:
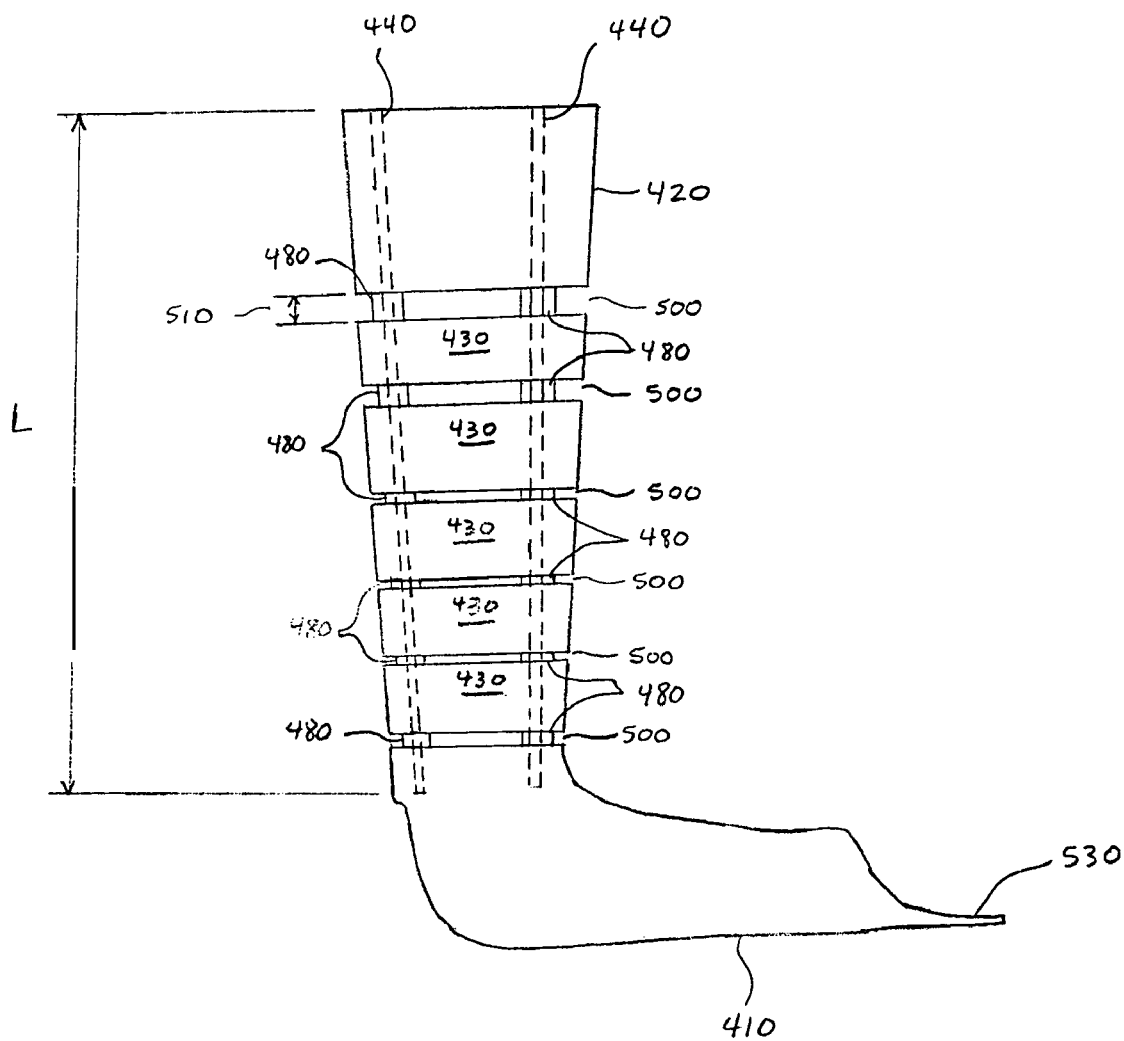
FIG. 17 is a side view of an ankle-foot orthosis according to a fourth embodiment of the present invention.

A third embodiment of the present invention is illustrated in FIG. 13. In such an embodiment, a hinge 310 is provided between a foot shell 320 and a lowermost segment 330, wherein one end of the hinge 310 is inserted into an opening 340 extending vertically through a posterior portion of a foot shell 320 and a second end is inserted into a passageway 350 extending vertically through a lower portion of the lowermost segment 330. A lower end of a strut 360 occupies an upper portion of the passageway 350 in the lowermost segment 330. Alternately, the hinge 310 can be located between any two adjacent segments 330. The hinge 310 can also be disposed between a calf shell 370 and the uppermost segment 330. Further, it is within the scope of the present invention that more than one hinge 310 be used.

The hinge 310 eliminates essentially all stiffness of the orthosis in both dorsiflexion and plantar flexion at a location where the hinge 310 is disposed, until, in dorsiflexion, front edges 400 of the segment 330 above the hinge 310 contacts front edges 395 of the foot shell 320. Additionally, the orthosis includes an adjustment mechanism (not shown) similar to the adjustment mechanism 200 described above, such as a threaded rod 220 and locknut 220 combination or a twist draw mechanism 230, to adjust the stiffness of the orthosis.

Referring to FIGS. 13-16, elastic members 380 can be provided, which extend through openings 390 formed in each of the calf shell 370, foot shell 320, and segments 330. The elastic members 380 attach to the calf shell 370 at one end and the foot shell 320 at an opposing end, but otherwise extend freely and unrestrained through the openings 390. The elastic members 380 are formed from any suitable elastomeric material, such as, for example only, rubber. The elastic members 380 provide a dorsiflexion bias sufficient, for example, to counteract the weight of the user's foot.

As a result of the hinge 310 and elastic members 380, the user is able to easily articulate the foot in plantar flexion. A user is also easily able to articulate the foot in dorsiflexion until the front edges 395 of the foot shell 320 contact front edges 400 of the lowermost segment 330. Thereafter, resistance to dorsiflexion motion increases as the segments 330 begin to contact each other at respective front edges 400. An orthosis of this type can assist users such as those who suffer from severe calf and hip weakness as well as low spasticity.

Figure 18:
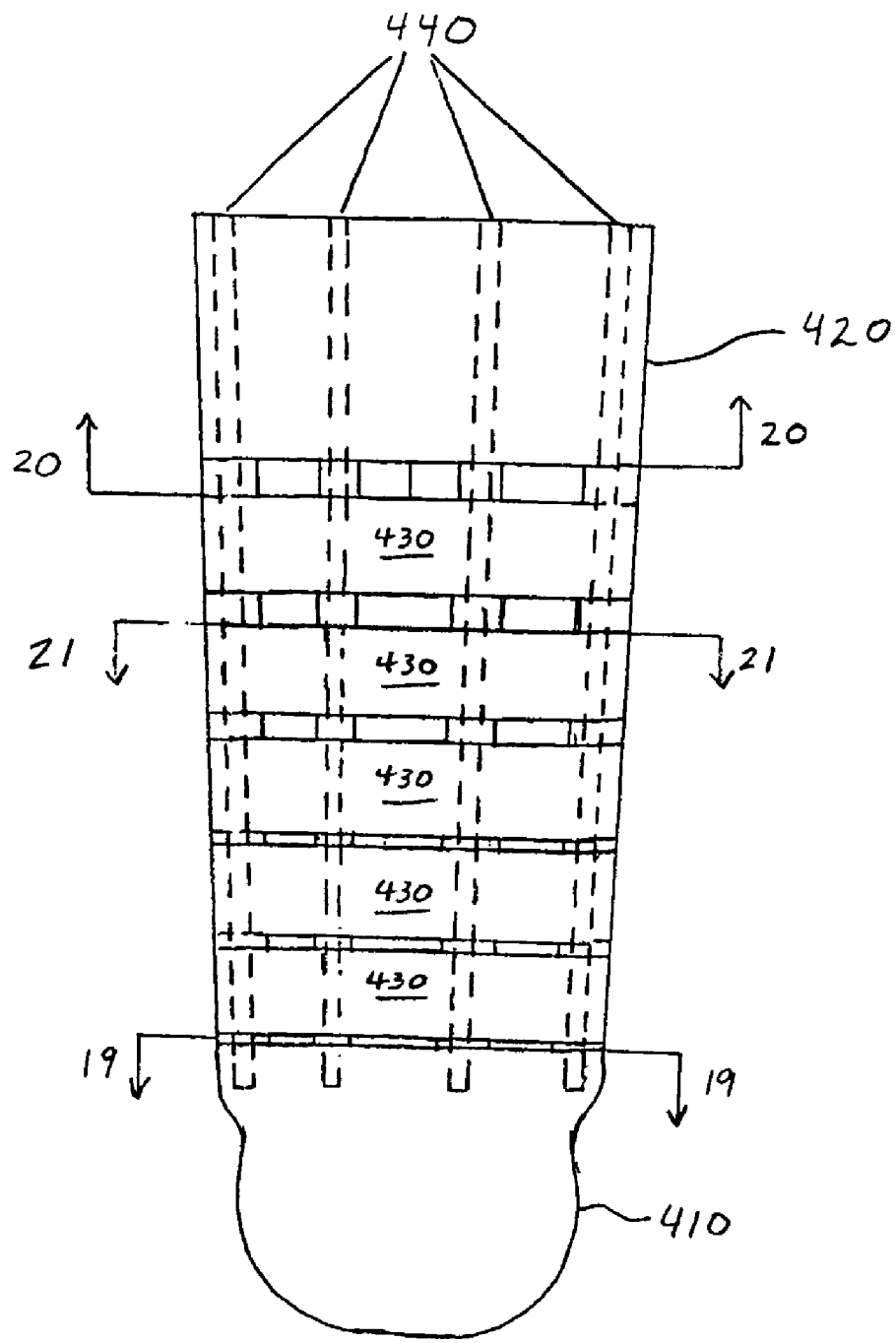
FIG. 18 is a back view of an ankle-foot orthosis shown in FIG. 17.
Figure 19:
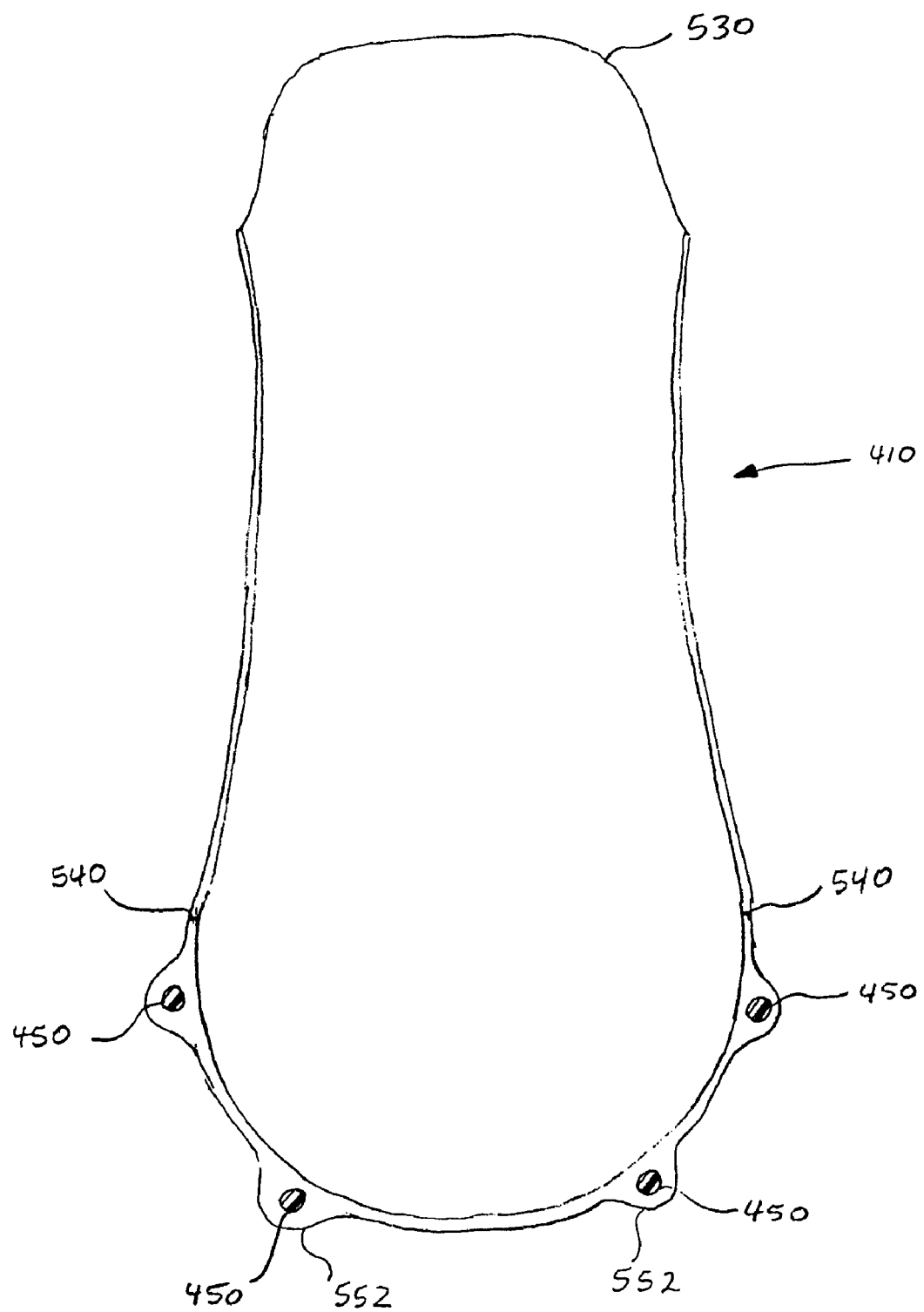
FIG. 19 is a view taken along line 19-19 in FIG. 18.
Figure 20:
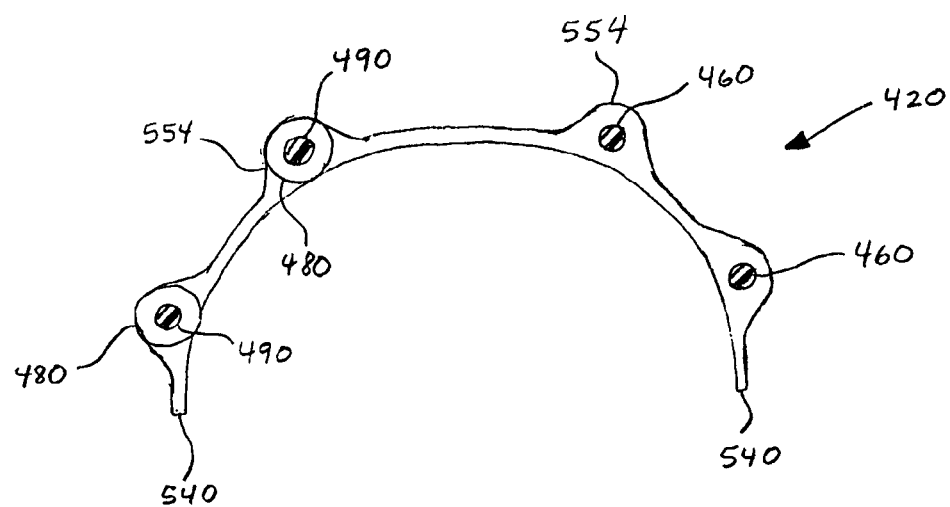
FIG. 20 is a view taken along line 20-20 in FIG. 18.
Figure 21:
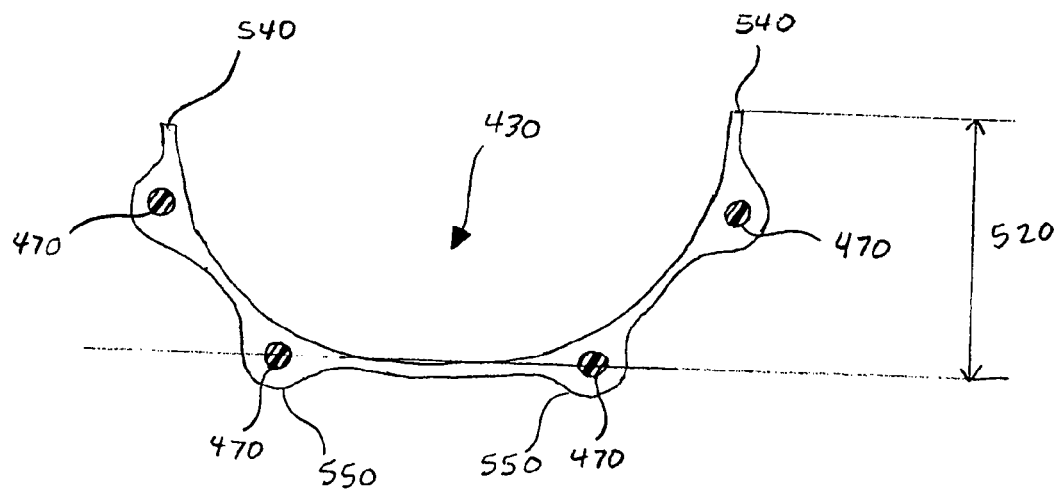
FIG. 21 is a view taken along line 21-21 in FIG. 18.

A fourth embodiment of the present invention includes a plurality of struts 440. FIGS. 17-21 illustrate an orthosis having a foot shell 410, a calf shell 420, segments 430, and struts 440. The struts 440 can be formed from the same types of materials described above for a single strut and operate in essentially the same fashion as a single strut. Additionally, each of the plurality of struts 440 can have a cross-section of any shape. Referring to FIGS. 18, 19, and 20, a lower end of each strut 440 is inserted into vertically extending openings 450 provided in a back portion of the foot shell 410, and an upper end is inserted into vertically extending passageways 460 provided in a back portion of the calf shell 420. Referring to FIGS. 18 and 21, the struts 440 retain the segments 430 by extending through vertically extending passageways 470 provided in a back portion thereof. The foot shell 410 and the calf shell 420 are fixably attached to the struts 440 by any one of fasteners, an adhesive, an interference fit, being insert molded therein at the time of manufacture, or any other manner now known or hereafter developed. Additionally, while an exemplary embodiment having four struts 440 is shown in FIGS. 17-21, it is envisioned that the present invention can have any number of struts.

Each strut 440 retains a plurality of spacers 480 by extending through openings 490 provided in a central portion of the spacers 480. The spacers 480 are provided between each segment 430, the uppermost segment 430 and the calf shell 420, and the lowermost segment 430 and the foot shell 410. The spacers 480 form gaps 500 having a gap width 510 and a gap length 520, as explained above. An orthosis of the present embodiment can also include an adjustment mechanism (not shown), such as a threaded rod 220 and locknut 220 combination or a twist draw mechanism 230, to adjust the gap widths 510 and, therefore, the stiffness of the orthosis. Additionally, the orthosis may include a liner (not shown) secured to an inner surface of at least one of the foot shell 410, calf shell 420, and the segments 430; an optional toe extension 530 attached to a front end of the foot shell 410; and straps (not shown), similar to straps 170 and 180 described above, provided on the calf shell 420 and foot shell 410 for securing the orthosis to a user's lower leg.

An orthosis having a plurality of struts operates in a similar fashion as the orthosis having a single strut. A flexing portion of the orthosis comprising the struts 440, the calf shell 420, the segments 430, and spacers 480 forms a beam having an effective length L, shown in FIG. 17. As the user's foot dorsiflexes, the gap widths 510 of gaps 500 progressively decrease along the gap length 520, compressing the spacers 480, wherein the greatest decrease in the gap width 510 occurs at the front edges 540. Because the gap widths 510 of the gaps 500 at a lower end of the orthosis are smaller than the gap widths 510 higher up, the front edges 540 of the lowermost segment 430 and foot shell 410 begin contacting each other sooner, changing the effective length L of the beam. The change in effective length L causes an increase in stiffness according to beam bending principles known to those of ordinary skill in the art. As the gaps 500 higher up continue to close at the front edges 540, the effective length L continues to progressively decrease making the orthosis stiffer, creating a gradual dorsiflexion stop, and reducing the magnitude of any forces transmitted through the user's body.

Referring to FIGS. 19-21, in plantar flexion, a rear edge 550 of the lowermost segment 430 is forced towards a rear edge 552 of the foot shell 410. Similarly, the rear edges 550 of adjacent segments 430 are also forced towards each other. Further, the rear edge 550 of the lowermost segment 430 is forced towards a rear edge 554 of the calf shell 420. As a result, the corresponding gap widths 510 narrow, compressing the associated spacers 480. Initially, the lowermost gap 500 adjacent to the foot shell 410 and having the smallest gap width 510 decreases until the spacer 480 provided therein can no longer be compressed. Next, the gap 500 immediately above stops closing because the spacer 480 provided therein can also no longer be compressed. Thereafter, the gaps 500 thereabove similarly stop closing in order, beginning with the lower, narrower gaps 500 and finishing with the larger gaps 500 near the calf shell 420. As a result, the effective length L of the flexing portion decreases with increased plantar flexion, causing the orthosis to progressively become stiffer, creating a gradual plantar flexion stop, and reducing the magnitude of any forces transmitted through the user's body.

Figure 24:
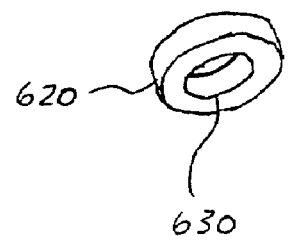
FIG. 24 is a perspective view of a spacer of the ankle-foot orthosis shown in FIG. 22.
Figure 26:
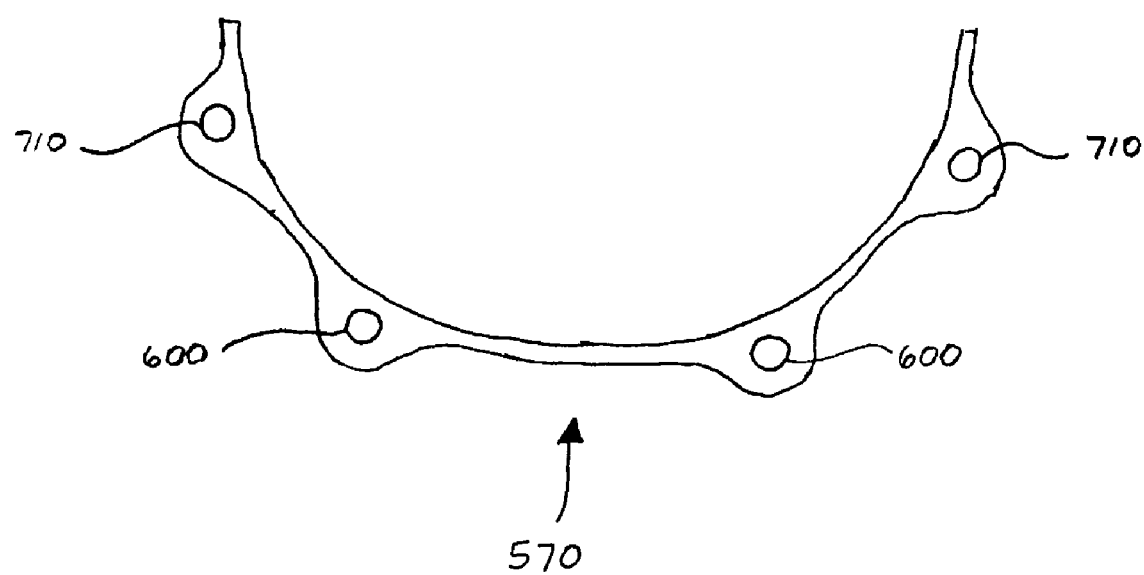
FIG. 26 is a view taken along line 26-26 in FIG. 23.

An orthosis having a plurality of struts can optionally include a hinge 660. FIGS. 22-27 illustrate an orthosis comprising a foot shell 560, a calf shell 570, and a plurality of segments 580 provided therebetween. Struts 590 extend from the calf shell 570 to the lowermost segment 580 by passing through openings 600 and passageways 610 provided therein, respectively. One end of the struts 590 is secured to the calf shell 570 while an opposing end is attached to the lowermost segment 580 above and adjacent to the foot shell 560. A plurality of spacers 620 are retained by the struts 590 and are disposed between adjacent segments 580 and the uppermost segment 580 and the calf shell 570. FIG. 24 illustrates a spacer 620 having a central opening 630 formed therein. The struts 590 pass through the openings 630 in each spacer 620. Gaps 640 having a gap width 650 substantially corresponding to a thickness of the spacers 620 are formed between adjacent segments 580, and the uppermost segment 580 and the calf shell 570.

Figure 22:
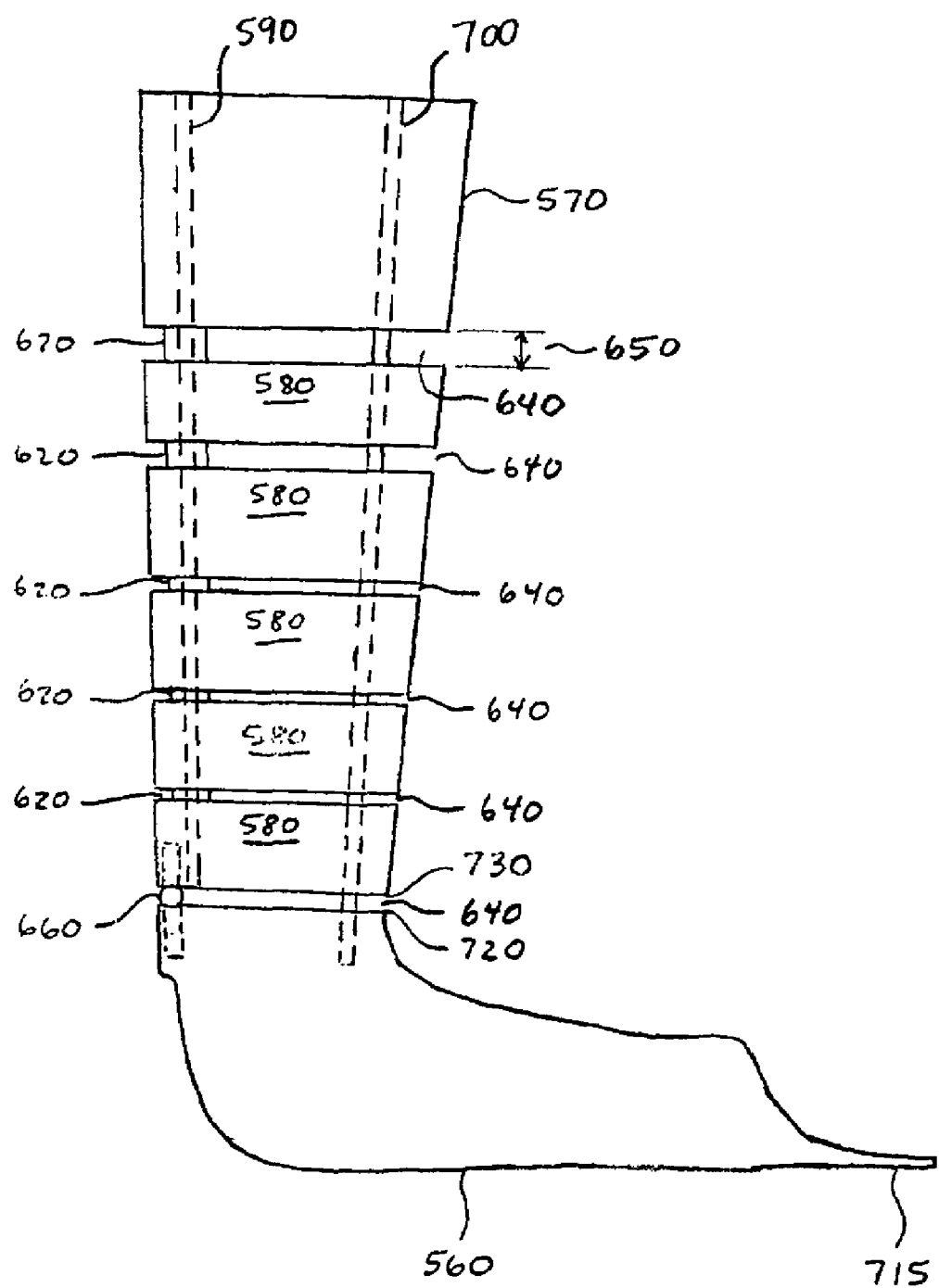
FIG. 22 is a side view of a fifth embodiment of an ankle-foot orthosis according to the present invention.
Figure 23:
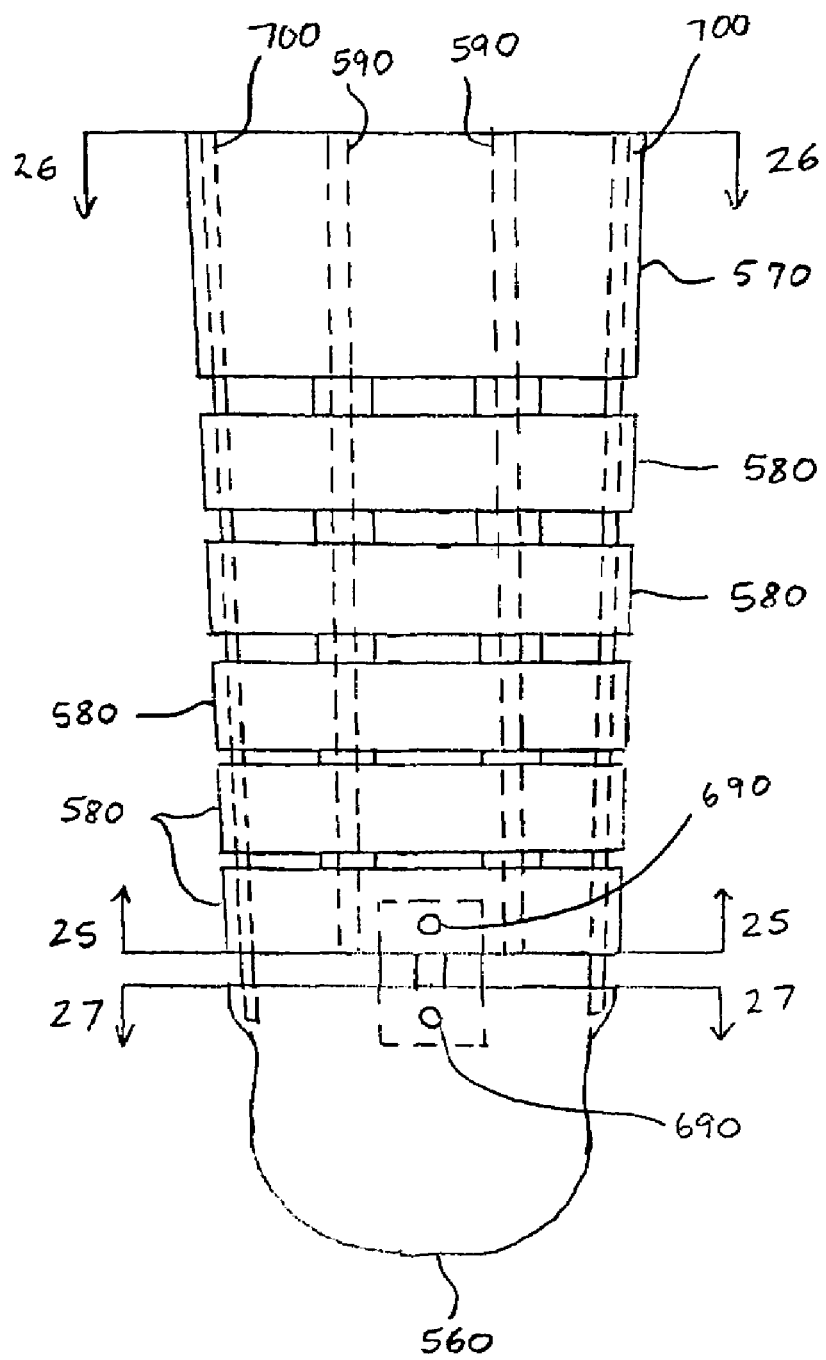
FIG. 23 is a back view of the ankle-foot orthosis shown in FIG. 22.
Figure 25:
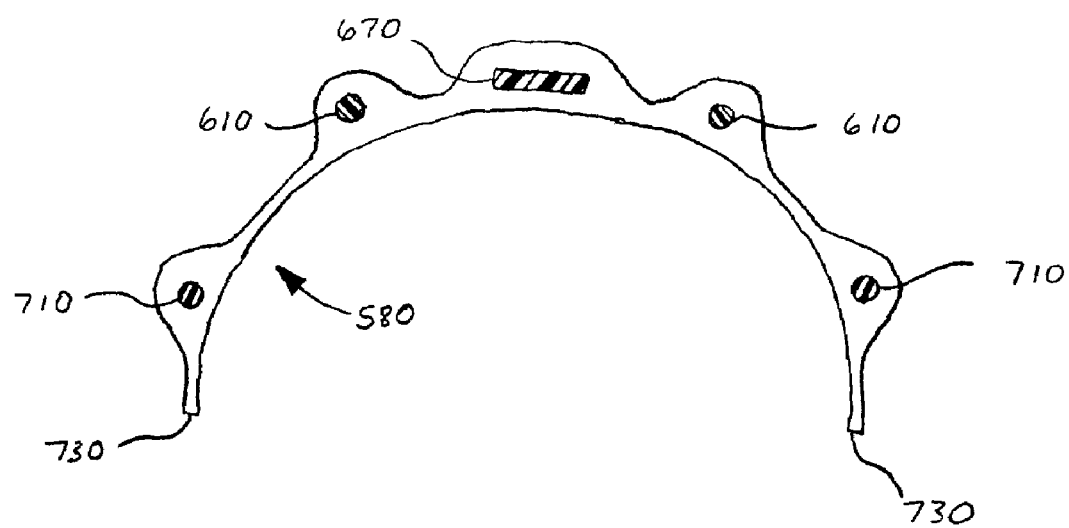
FIG. 25 is a view taken along line 25-25 in FIG. 23.
Figure 27:
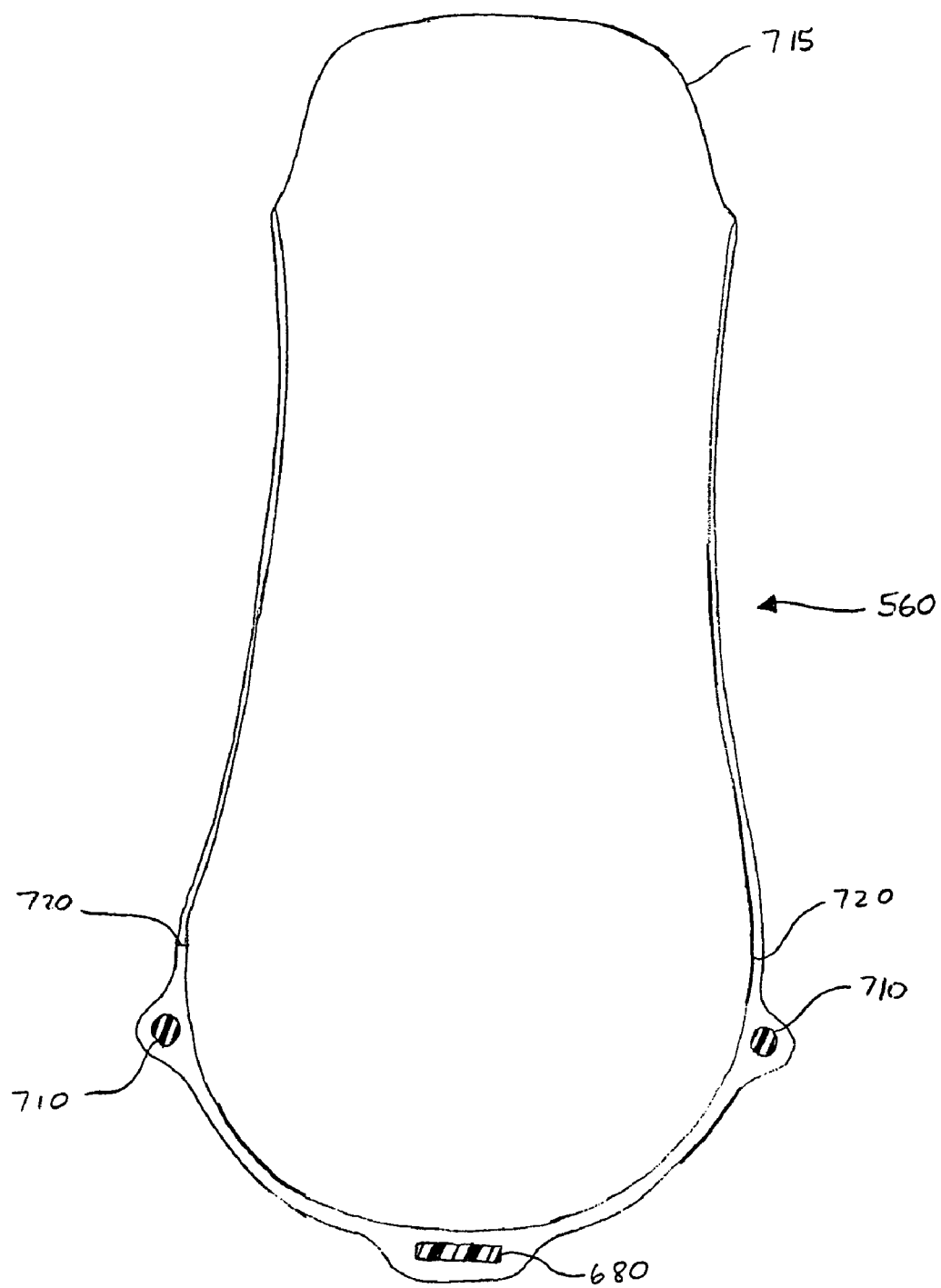
FIG. 27 is a view taken along line 27-27 in FIG. 23.

The gap widths 650 of the gaps 640 increase in size with increasing distance from the foot shell 560. A hinge 660 is provided in a gap 640, such as the gap 640 formed between the foot shell 560 and the lowermost segment 580. Referring to FIGS. 22, 25, and 27, one end of the hinge 660 is inserted into a vertically extending opening 670 in a lower surface of the lowermost segment 580 and a second end is inserted into a vertically extending opening 680 in an upper surface of the foot shell 560. The hinge 660 is secured to the orthosis with fasteners 690 or an adhesive, for example. The hinge 660 eliminates substantially all stiffness of the orthosis in both dorsiflexion and plantar flexion at a location where the hinge 660 is disposed, until, in dorsiflexion, front edges 730 of the segment 580 above the hinge 660 contacts front edges 720 of the foot shell 560.

The orthosis also includes elastic members 700 that extend from the calf shell 570 to the foot shell 560. The elastic members 700 extend through openings 710 provided in each of the calf shell 570, foot shell 560, and segments 580. An end of the elastic members 660 are affixed to both the calf shell 570 and the foot shell 560, but otherwise extend freely and unrestrained through the openings 710. The elastic members 700 are formed from any suitable elastomeric material, such as rubber. Further, the elastic members 700 provide a dorsiflexion bias as described above and can assist users suffering from severe calf and hip weakness as well as low spasticity.

Additionally, the orthosis may include a liner (not shown), a toe extension 715, and straps, each of which performs a similar function as the corresponding features described above with respect to the first embodiment of the present invention. Discussion of these features is omitted herefrom to avoid redundancy.

An orthosis having a hinge 310 and a plurality of struts 590 operates identically to an orthosis having a hinge and only a single strut, as described with respect to the third embodiment of the present invention. Discussion of these features is omitted herefrom to avoid redundancy.

Figure 28:
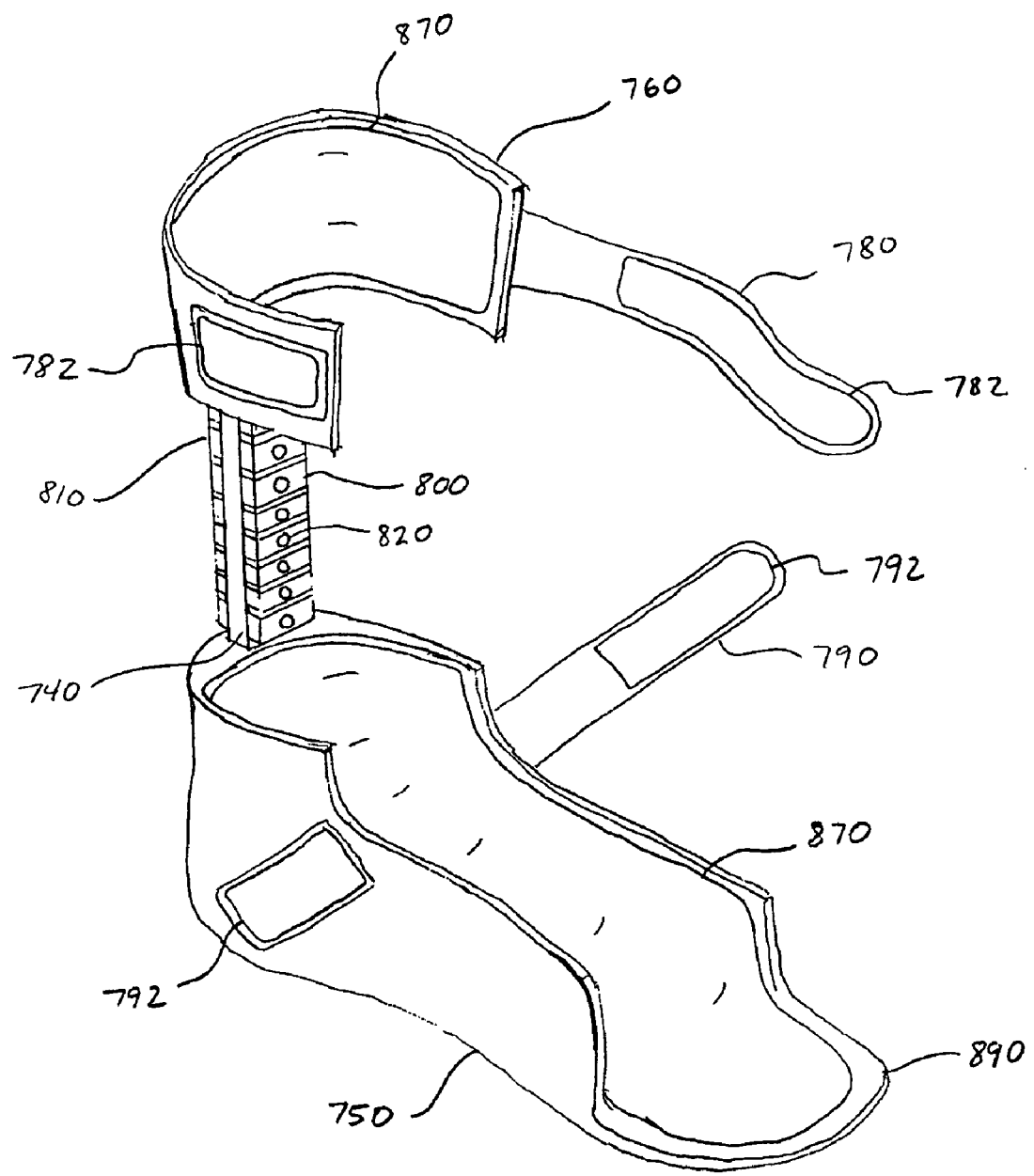
FIG. 28 is a perspective view of a sixth embodiment of the ankle-foot orthosis according to the present invention.
Figure 29:
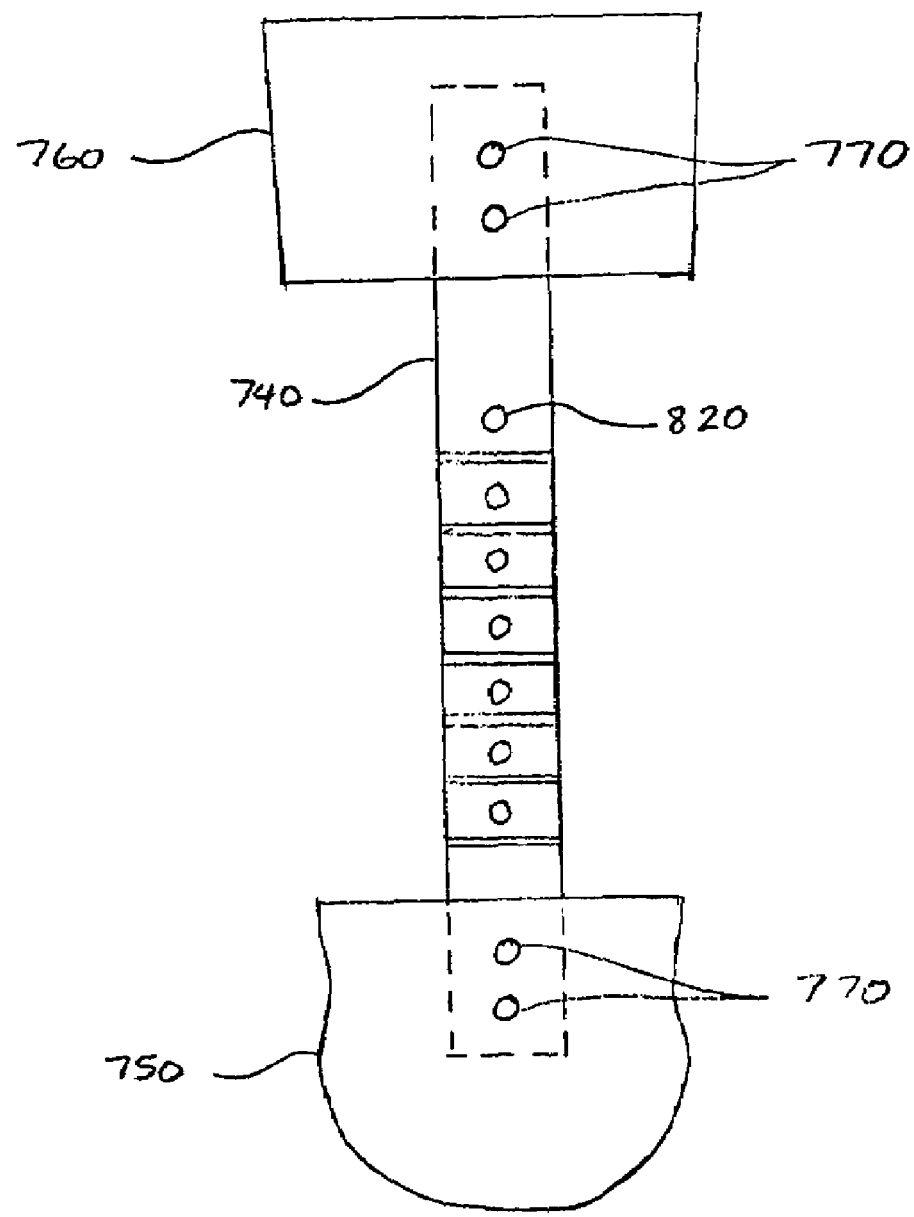
FIG. 29 is a back view of the ankle-foot orthosis shown in FIG. 28.
Figure 30:
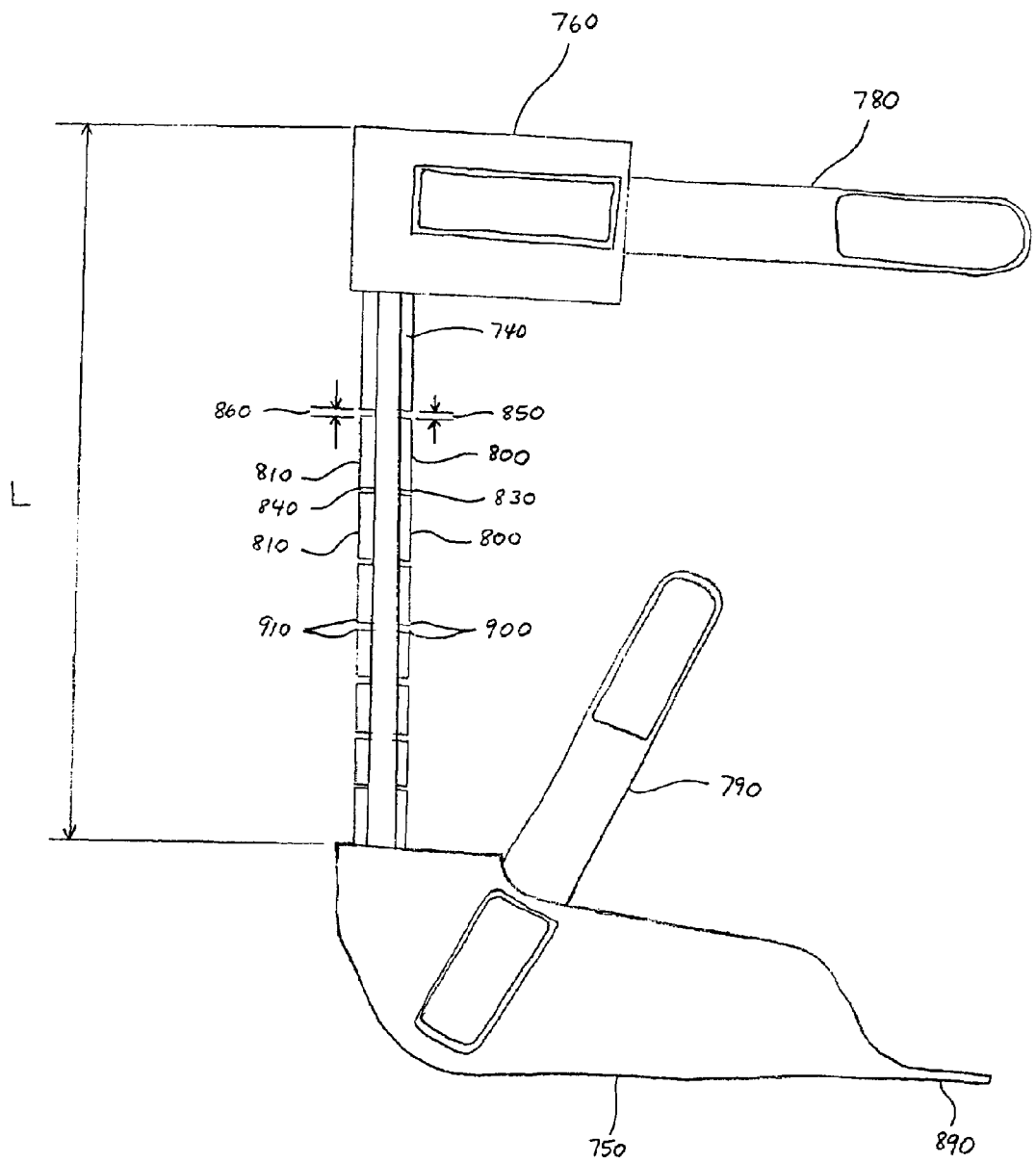
FIG. 30 is a side view of the ankle-foot orthosis shown in FIG. 28.

A sixth embodiment of the present invention is illustrated in FIGS. 28-30, wherein an orthosis comprises a strut 740 with a foot shell 750 provided at one end and a calf shell 760 provided on an opposite end. The foot shell 750 and calf shell 760 attach to the strut 740 with fasteners 770, an adhesive, or by insert molding, for example. The orthosis also includes straps 780 and 790, similar to straps 170 and 180 described above, attached to the calf shell 760 and foot shell 750, respectively, for securing the orthosis to a user's lower leg. As shown in FIGS. 28 and 29, a plurality of segments 800 and 810 are provided on anterior and posterior sides of the strut 740, respectively, and can be integrally formed therein or separately attached thereto using fasteners 820. Referring to FIG. 30, gaps 830 and 840 are formed between adjacent segments 800 and 810, respectively. The gaps 830 and 840 have gap widths 850 and 860, respectively, wherein the gap widths 850 and 860 are narrower at a lower end of the strut 740 and are progressively wider towards an upper end thereof. However, it is within the scope of the present invention that the gap widths 850 and 860 can be any size along the length of the strut 740. A liner 870 can also be added to an inner surface of the calf shell 760 and foot shell 750, such as with an adhesive. The liner 870 is formed from a thin padding material that provides a comfortable form fit and cushioning. Further, a toe extension 890 can be attached at a front end of the foot shell 750 to support the user's toes.

The orthosis fits to the user's lower leg, wherein an upper surface of the foot shell 750 can be generically shaped or custom fit to a lower surface of the user's foot. A front surface of the calf shell 760 is configured to abut a posterior surface of the lower leg. The strap 780 extends over an anterior surface of the lower leg and attaches to the calf shell via an attachment mechanism 782. The strap 790 extends over an upper foot surface and attaches to the foot shell 750 via an attachment mechanism 792. In a preferred embodiment, the attachment mechanisms 782 and 792 are a hook and loop closure. However, it is within the scope of the invention that the attachment mechanisms 782 and 792 be snap fasteners, a buckle, or any structure capable of securing the calf shell 760 to the user's lower leg. A piece of footwear is then placed onto the foot. Optionally, the orthosis is integrated into a piece of footwear, such as boots.

Referring to FIG. 30, a flexing portion of the orthosis comprising the strut 740, the calf shell 760, and segments 800 and 810 forms a beam having an effective length L. As the foot dorsiflexes, the gaps 830 begin to close as front edges 900 of adjacent segments 800 move towards each other. Because the gaps 830 near the lower end of the strut 740 are smaller than those towards the upper end, the lower gaps 830 close first. As dorsiflexion increases, the next higher gap 830 closes and so on. As a result, the effective length L decreases as each gap 830 closes, making the orthosis gradually stiffer and creating a gradual dorsiflexion stop. Consequently, the orthosis reduces the magnitude of forces transmitted into the user.

In plantar flexion, the gaps 840 near the lower end of the strut 740 close first as rear edges 910 of adjacent segments 810 move towards each other. Because the gaps 840 near the lower end of the strut 740 are smaller than those towards the upper end, the lower gaps 840 close first. As plantar flexion increases, the next higher gap 840 closes and so on. As a result, the effective length L decreases as each gap 840 closes, making the orthosis gradually stiffer and creating a gradual plantar flexion stop. As a result, the orthosis reduces the magnitude of forces transmitted through the user's body.

While there has been described what are at present considered to be preferred embodiments of the present invention, it will be understood that various modifications may be made thereto, and it is intended that the appended claims cover all such modifications as fall within the scope of the invention. Other modifications will be apparent to those skilled in the art.

What is claimed is:

1. An ankle-foot orthosis comprising:
   at least one strut member;
   a calf shell disposed at an upper end of the at least one strut member;
   a foot shell disposed at a lower end of the at least one strut member;
   a plurality of segments disposed on the at least one strut member and between the calf and foot shells; and
   a plurality of gaps, wherein a gap is formed between adjacent segments, a gap is formed between an uppermost segment and the calf shell, and a gap is formed between a lowermost segment and the foot shell.

2. The orthosis according to claim 1, wherein each segment of the plurality of segments has a U-shaped cross-section or a substantially rectangular cross-section.

3. The orthosis according to claim 1, wherein each segment of the plurality of segments is either integrally formed about the at least one strut member or secured to the at least one strut member by fasteners.

4. The orthosis according to claim 1, wherein each segment of the plurality of segments includes a passageway extending therethrough, and wherein the passageway is configured to receive the at least one strut member therein.

5. The orthosis according to claim 1, further comprising:
a dorsiflexion stop; and
a plantar flexion stop.

6. The orthosis according to claim 5, wherein the dorsiflexion stop is defined by front edges of the adjacent segments engaging each other.

7. The orthosis according to claim 6, wherein the at least one strut member further comprises an upper portion and a lower portion, wherein the gaps formed in the lower portion of the at least one strut member are narrower relative to the gaps formed in the upper portion of the at least one strut member, and wherein a degree of rigidity of the dorsiflexion stop increases as the front edges of adjacent segments in the upper portion of the at least one strut member engage each other.

8. The orthosis according to claim 5, wherein the plantar flexion stop is defined by rear edges of the adjacent segments engaging each other.

9. The orthosis according to claim 8, wherein the at least one strut member further comprises an upper portion and a lower portion, wherein the gaps formed in the lower portion of the at least one strut member are narrower relative to the gaps formed in the upper portion of the at least one strut member, and wherein a degree of rigidity of the plantar flexion stop increases as the rear edges of the adjacent segments in the upper portion of the at least one strut member engage each other.

10. The orthosis according to claim 1, wherein the at least one strut member further comprises an upper portion and a lower portion, and wherein the gaps formed in the lower portion of the at least one strut member are narrower relative to the gaps formed in the upper portion of the at least one strut member.

11. The orthosis according to claim 1, further comprising:
an adjustment mechanism for expanding or narrowing a height of each gap, wherein narrowing the height of each gap increases a rigidity of the orthosis, and wherein expanding the height of each gap decreases the rigidity of the orthosis.

12. The orthosis according to claim 11, wherein narrowing the height of each gap reduces a range of motion of the orthosis, and wherein expanding the height of each gap increases the range of motion of the orthosis.

13. The orthosis according to claim 11, wherein the adjustment mechanism is either a threaded rod and locknut combination or a twist draw mechanism.

14. The orthosis according to claim 1, further comprising:
at least one spacer disposed within each gap and which encompasses a corresponding portion of the at least one strut member,
wherein the spacer is compressed during dorsiflexion and plantar flexion as edges of the adjacent segments engage each other to define a stop, and
wherein the compressed spacer increases a rigidity of the orthosis.

15. The orthosis according to claim 14, further comprising:
an adjustment mechanism for expanding or narrowing a height of each gap to increase or decrease a rigidity of the orthosis.

16. The orthosis according to claim 15, wherein narrowing the height of each gap reduces a range of motion of the orthosis, and wherein expanding the height of each gap increases the range of motion of the orthosis.

17. The orthosis according to claim 1, wherein the orthosis further comprises at least one spacer integrally formed on a corresponding segment, and wherein each spacer includes at least one rounded edge that rollingly engages a neighboring segment.

18. The orthosis according to claim 1, further comprising:
a liner secured to at least one of an anterior surface of the foot shell, anterior surfaces of the plurality of segments, and an anterior surface of the calf shell.

19. The orthosis according to claim 1, further comprising:
at least one strap for securing the ankle-foot orthosis to a user.

20. The orthosis according to claim 19, wherein the ankle-foot orthosis further includes an attachment mechanism for removably attaching the at least one strap to at least one of the calf shell, the foot shell, and the plurality of segments.

21. The orthosis according to claim 20, wherein the attachment mechanism is one of a hook and loop fastener, a buckle, and a snap fastener.

22. The orthosis according to claim 1, further comprising:
at least one hinge provided between at least one of a lowermost segment and the foot shell, the adjacent segments, and an uppermost segment and the calf shell; and
at least one elastic member extending from the calf shell to the foot shell to provide a dorsiflexion bias.

23. The orthosis according to claim 22, wherein a first end of the at least one elastic member is secured to the foot shell, a second end of the at least one elastic member is secured to the calf shell, and a remaining portion of the at least one elastic member extends through aligned passageways provided in the calf shell, the foot shell, and the plurality of segments.

24. A method of providing an orthosis comprising at least one strut member, a calf shell, a foot shell, and a plurality of segments disposed between the calf shell and foot shell with gradual stops in dorsiflexion and plantar flexion, the method comprising the steps of:
forming gaps in the orthosis between at least one of two adjacent segments, an uppermost segment and the calf shell, and a lowermost segment and the foot shell, wherein the gaps formed in a lower portion of the at least one strut member are narrower than gaps formed in an upper portion of the at least one strut member; and
manipulating the orthosis in one of dorsiflexion and plantar flexion, wherein edges of adjacent segments forming the gaps in the lower portion of the at least one strut member engage before edges of adjacent segments forming the gaps in the upper portion of the at least one strut member engage each other.

* * * * *